United States Patent [19]

Vinci et al.

[11] Patent Number: 5,849,541
[45] Date of Patent: Dec. 15, 1998

[54] DNA ENCODING TRIOL POLYKETIDE SYNTHASE

[75] Inventors: Victor A. Vinci, Indianapolis, Ind.; Michael J. Conder, Harrisonburg, Va.; Phyllis C. McAda; Christopher D. Reeves, both of Woodenville, Wash.; John Rambosek, Seattle, Wash.; Charles Ray Davis, Lynnwood, Wash.; Lee E. Hendrickson, Carnation, Wash.

[73] Assignee: Merck & Co., Inc., Rahway, N.J.

[21] Appl. No.: 637,640

[22] PCT Filed: Oct. 28, 1994

[86] PCT No.: PCT/US94/12423

§ 371 Date: Aug. 23, 1996

§ 102(e) Date: Aug. 23, 1996

[87] PCT Pub. No.: WO95/12661

PCT Pub. Date: May 11, 1995

Related U.S. Application Data

[63] Continuation of Ser. No. 148,132, Nov. 2, 1993, abandoned.
[51] Int. Cl.$^6$ .............................. C12P 19/34; C12P 17/06; C12N 9/00; C07H 21/04
[52] U.S. Cl. .................. 435/91.1; 435/69.2; 435/125; 435/183; 435/254.11; 435/254.3; 435/254.5; 435/254.6; 435/320.1; 536/23.2; 536/24.32
[58] Field of Search ................................. 435/69.2, 91.1, 435/125, 254.3, 254.5, 254.6, 320.1, 183; 536/23.2, 24.32

[56] References Cited

U.S. PATENT DOCUMENTS

| | | | |
|---|---|---|---|
| 4,231,938 | 11/1980 | Monaghan et al. | 549/292 |
| 4,346,227 | 8/1982 | Terahara et al. | 560/119 |
| 5,151,365 | 9/1992 | Dombrowski et al. | 435/256.1 |
| 5,159,104 | 10/1992 | Dabora et al. | 560/119 |
| 5,182,298 | 1/1993 | Helms et al. | 514/455 |
| 5,198,345 | 3/1993 | Gwynne et al. | 435/69.1 |
| 5,252,474 | 10/1993 | Gewain et al. | 435/172.3 |
| 5,362,638 | 11/1994 | Dahiya | 435/125 |

FOREIGN PATENT DOCUMENTS 0 556 699 A1  8/1993  European Pat. Off. .

OTHER PUBLICATIONS

Buckland, et al., "Production of lovastatin, an inhibitor of cholesterol accumulation in humans", Novel Microbial Products for Medicine and Agriculture, Ch. 19, pp. 161–169 (1989).

Hopwood, et al., "Molecular Genetics of Polyketides and its Comparison to Fatty Acid Biosynthesis", Annu. Rev. Genet., 1990, 24, pp. 37–66.

Moore, et al., "Biosynthesis of the Hypocholesterolemic Agent Mevinolin . . . ", J. Am. Chem. Soc., 1985, 107, pp. 3694–3701.

Endo, et al., "Dihydromonacolin L and Monacolin X, New Metabolites . . . ", The Journal of Antibiotics, vol. XXXVIII, No. 3, pp. 321–327, 1985.

Endo, et al., Monacolin M, New Inhibitor of Cholesterol Bisoynthesis, The Journal of Antibiotics, Dec. 1896, vol. XXXIX, pp. 1670–1673.

Springer, et al., "Terretonin, a Toxic Compound from Aspergillus terreus", J. Org. Chem., vol. 44, No. 26, pp. 4852–4854 (1979).

Aria, et al., "Pravastatin Sodium (CS–514) A Novel Cholesterol Lowering Agent . . . ", Sankyo Kenkyusho Vempo, 40, 1–38 (1988).

Drugs of the Future, vol. 12, No. 5, 1987 "Eptastatin Sodium".

Mayorga, et al., "The Developmentally Regulated Aspergillus . . . ", Mol. Gen. Genet., 235(2–3): 205–212 (Nov. 1992).

Leadley, et al., "The Erythromycin–Producing Polyketide Synthase", Biochem. Soc. Trans. 21 (1): 218–222, (Feb. 1993).

Cortes, et al., "An Unusually Large Multifunctional Polypeptide . . . ", Nature, 348, 176–178 (Nov. 1990).

Bevitt, et al., "6–Deoxyethromolide–B Synthase . . . ", Eur. J. Biochem., 204: 39–49 (Feb. 1992).

Beck, et al., "The Genetic and Biochemical Basis of Polyketide Metabolism . . . ", Planta Med. 57(7) (Suppl. 1): 536–543 (Oct. 1991).

*Primary Examiner*—Robert A. Wax
*Assistant Examiner*—Elizabeth Slobodyansky
*Attorney, Agent, or Firm*—Michael D. Yablonsky; Jack L. Tribble

[57] ABSTRACT

DNA encoding triol polyketide synthase (TPKS) from *Aspergillus terreus* has been isolated, purified and sequenced. Expression vectors comprising said DNA, cells transformed with the expression vectors, and processes employing the transformed cells are provided.

10 Claims, 30 Drawing Sheets

| | | | | |
|---|---|---|---|---|
| CTGCAGTCAA | CGGATCACTT | ACCATTGCTG | TCGCCAAAAA | TATCCGTGAT | AATCCCGCTG | 60
| GCTTCATTGG | CAAGAGGCTT | GACGTACTTG | GGAGCTTGGG | TCTGGAACTG | GTTCATAACC | 120
| ACCTTGGTGA | TGAGATGTGC | ATCCCTCGTG | ACTTCCTTGA | ATCCATCGAA | TCCGGGAAGA | 180
| TGAGAGTGAA | AGTCCTGATG | AGAGCACGAA | GATCAGTAAG | TCAGGTCCTC | ACAGCGGAAG | 240
| CAGTTGCAAA | GAACGGTGGA | CTCCTTACCG | TGCCCAAGAA | CTTGTACATA | CAGAGCTCTT | 300
| TCATCTTGCG | AAACTCATCG | GCCATAGAGG | AGGGAAGAAT | GGTGCAGTAC | CCAGAGTCGA | 360
| CTATGAACCG | AATGGGCTTA | TCATTTGCG | AGAACCAGCT | CTCAATCCAT | GACGGTGCAT | 420
| TCGCATCAAA | ATCCCGTTTG | GCCCTCATGG | TCGTCAGTTC | CCACCATGTT | TTCGGATTGA | 480
| ACACCGGCAG | ATCAGATCTC | CGGCCACTCG | AGCACAGGTA | AAGAAGAAGG | CATAGTAGCC | 540
| CCGCACTGGT | AGTGACCAAG | GGCGCAAACC | ACGAGCCATG | TTGCTGCGTG | TCATTCCAAG | 600
| CCAGCGACAG | AAGGTGGTGC | GGCTGTGTGA | GCGGTCGAC | AGTCATGGCT | AGGAGACCAG | 660
| GTGTGGTTGA | GGGATAAGAT | ATCGAGAGTG | ATGTGAGCAA | AAGATCCGGG | AAAGGTCGCG | 720

FIG. 1A

```
AAGGAAAGGG CGTCTCTCTT ACCAAGAAAG TCTGTTCCCT ATCATGCAAT CACCGCTTGC    780
TGTACGGTGG TGATGATGCT GGGATGGTGG TGGGTCCCCA CCGAATAACG CCGGACAGCT    840
GTTGAAGCCG AATGACGCCG GCAGGCCAAA AGAACCCTAC CTTCACTTAC TCAATCGGCG    900
CTTCCCCTCC TATCACCAAA TCGGATGTAA ATGGACGGGC CTTAATAGCG ACCGGCCGGG    960
CCGGGAATCC CCAAACGTAG ATAGATAGGC ATAGACCCGA AATCTTTGGC CCGGCATACA   1020
TGAGCACAGG AAGTTTCACG CGACGGCGCC TTTCCTGCCT CAGCTTCAAT CCAAGCTCAC   1080
GAGTTCTGTC GCCTCTATCA GTCGTGCAAT TGTCCTACTG CAAACAGCAT GGCTCAATCT   1140
ATGTATCCTA ATGAGCCTAT TGTCGTGGTC GGCAGTGGTT GTCGCTTCCC TGGTGACGCC   1200
AACACACCCT CCAAGCTCTG GGAGCTACTC CAGCATCCTC GCGATGTGCA GAGTCGAATC   1260
CCCAAAGAAC GATTTGACGT CGACACATTT TATCACCCGG ACGGAAGCA CCACGGGCGA    1320
ACAAATGCAC CCTACGCCTA TGTTCTCCAA GACGATCTGG GCGCCTTCGA TGCGGCCTTC   1380
TTCAATATCC AGGCTGGAGA GGCCGAGAGT ATGGACCCCC AGCACCGGCT GTTGCTGGAG   1440
```

FIG. 1B

```
ACGGTGTACG  AGGCCGTAAC  GAATGCTGGA  ATGCGTATCC  AGGATCTGCA  GGGAACTTCG   1500
ACTGCTGTTT  ACGTCGGGGT  GATGACGCAC  GACTATGAGA  CTGTCTCAAC  CCGCGACCTG   1560
GAGAGCATCC  CCACCTACTC  GGCGACGGGT  GTCGCGGTCA  GTGTTGCGTC  CAACCGCATC   1620
TCGTATTTT   TTGACTGGCA  TGGACCAAGT  GTAAGTCACC  CAATATCGTG  TAGCAGTCTA   1680
ATCATGCTCT  AACGGACCGG  GATGGTTGAA  AGATGACGAT  CGATACGGCA  TGCAGCTCGT   1740
CGTTGGTTGC  CGTTCATCTG  GCGGTGCAAC  AGCTACGGAC  GGGTCAAAGC  TCCATGGCAA   1800
TTGCTGCGGG  TGCGAATCTG  ATTCTGGGGC  CGTCCTTGAA  AGCAAATTGA  1860
GCATGCTATC  CCCCTCGGGT  CGATCCCGCA  TGTGGGACGC  CGGAGCTGAC  GGCTATGCCA   1920
GAGGCGTGAG  TGTTTCTTGA  GCTCGTAGAT  GACAGTTCCC  ATCGCTGACC  GTGATCAGGA   1980
AGCTGTTTGC  TCTGTAGTGT  TGAAGACATT  GAGTCAAGCC  TTGCGCGATG  GGGACACGAT   2040
```

FIG. 1C

```
TGAATGTGTC ATCCGAGAAA CTGGGGTGAA TCAAGATGGC CGAACGACCG GAATTACGAT      2100
GCCGAACCAT AGTGCTCAGG AGGCACTCAT CAAGGCTACC TACGCCCAGG CTGGCCTTGA      2160
CATCACCAAG GCCGAGGACA GGTGCCAATT CTTCGAGGCT CATGGTCAGC AAAGAGAACC      2220
TGTTCTGTTG GCGCCCTGCA GCTGACATTC GTATGATAGG GACTGGTACT CCGGCCGGAG      2280
ATCCCCAGGA GGCGGAGGCC ATTGCAACAG CCTTCTTCGG CCACGAGCAG GTAGCACGCA      2340
GCGACGGAAA CGAGAGGGCC CCTCTGTTCG TGGGCAGTGC GAAAACTGTT GTCGGGCACA      2400
CCGAGGGCAC GGCCGGTCTG GCTGGTCTCA TGAAGGCGTC GTTCGCTGTC CGCCATGGGG      2460
TAATCCCCCC CAACCTGCTG TTCGACAAAA TCAGCCCGCG AGTCGCCCCA TTCTATAAAA      2520
ACCTGAGGAT TCCGACAGAA GCTACCCAAT GGCCAGCTCT CCCACCCGGA CAACCGCGCC      2580
GCGCCAGTGT CAACTCCTTT GGTAAGCGAG GATTGCCCGG AGGAACCCTC ACAAGTACTC      2640
```

FIG. 1D

```
GAATTAATGC TAACTGAACC GCGCCGATGG ACAGGATTCG GCGGCACGAA TGCGCATGCC  2700
ATTATTGAGG AATACATGGA GCCAGAGCAA AACCAGCTGC GAGTCTCGAA TAATGAGAC   2760
TGCCCACCCA TGACCGGTGT CCTGAGTTTA CCCTTAGTCC TCTCGGCGAA GTCCCAGCGC  2820
TCCTTAAAGA TAATGATGGA GGAGATGCTG CAATTCCTTC AGTCTCACCC CGAGATACAC  2880
TTGCACGACC TCACCTGGTC CTTACTGCGC AAGCGGGTCAG TTCTACCCTT CCGCCGGGCT  2940
ATTGTCGGCC ATAGTCATGA AACCATCCGC CGGGCTTTGG AGATGCCAT CGAGGATGGT   3000
ATTGTGTCGA GCGACTTCAC TACGGAGGTC AGAGGCCAGC CATCGGTGTT GGGAATCTTC  3060
ACCGGGCAGG GGGCGCAGTG GCCGGGGATG TTAAAGAATC TGATAGAGGC ATCGCCATAT  3120
```

FIG.1E

```
GTGCGGAACA TAGTGAGGGA GCTGGACGAC TCCCTGCAGA GCTTGCCGGA AAAATACCGG   3180
CCCTCGTGGA CGCTACTGGA CCAGTTCATG CTAGAAGGAG AGGCCTCCAA CGTCCAATAT   3240
GCTACTTTCT CCCAGCCATT ATGCTGCGCG GTGCAAATTG TCCTGGTCCG TCTCCCTGAA   3300
GCCGCGAGAA TACGATTCAC GGCTGTGTT GGACATAGCT CCGGCGAAAT TGCTTGCGCC   3360
TTTGCTGCCG GGCTCATCAG TGCCTCGTTG GCGATTCGGA TTGCTTACTT ACGTGGAGTC   3420
GTCTCGGCAG GGGGCGCCAG AGGCACACCG GGAGCCATGT TGGCCGCCGG GATGTCCTTT   3480
GAGGAAGCAC AAGAGATCTG CGAGTTGGAT GCCTTTGAGG GCCGCATCTG CGTGGCTGCC   3540
AGCAATTCCC CAGACAGTGT AACTTTCTCT GGCGACGCGA ACGCAATTGA TCACCTGAAG   3600
GGCATGTTGG AGGATGAGTC CACTTTTGCG AGACTGCTCA AGTCGATAC AGCGTACCAC   3660
```

FIG.1F

```
TCGCATCATA TGCTTCCATG TGCAGACCCA TATATGCAAG CCCTAGAAGA GTGTGGTTGT    3720
GCTGTTGCCG ATGCAGGTTC CCCAGCCGGA AGTGTACCCT GGTATTCGTC CGTGGACGCC    3780
GAGAACAGGC AAATGGCAGC AAGAGACGTG ACCGCCAAGT ACTGGAAAGA TAACTTAGTA    3840
TCTCCGGGTGC TATTCTCCCA CGCAGTGCAG CGGGCAGTCG TCACGCACAA GGCGCTGGAT    3900
ATCGGGATTG AAGTGGGCTG TCACCCAGCT CTCAAGAGCC CATGCCGTCGC TGGAGCCGAGG   3960
GATGTCCTAT CTGGGGTTGA CCTGGGCGTAT ACAGGTTGCT CTCTGGGAAA GGTTTGGTGC   4020
CTCGATTCAT TCTCTCGAGC ACTGGCATAT CTCTGGGGCG CCTGATCGGC AAAGAATGAT    4080
GATGCGGACG AGTTCATGCG TGCAGTCGCG CCTGTATGAG CTCCAGTTTC TGTGTCGAAG    4140
CTCCTACCGG CCTATCCATG GGACCGCTCT CGTCGCTACT GGTGGAATC CCGAGCAACT     4200
```

FIG. 1G

```
CGCCACCATC TTCGAGGGCC CAAGCCCCAT CTTCTATTAG GAAAGCTCTC CGAATACAGC    4260
ACTCCGCTAA GCTTCCAGTG GCTGAATTTT GTGCGCCCAC GAGACATTGA ATGGCTTGAT    4320
GGACATGCAT TGCAAGGCCA GACTGTCTTC CCTGCGGCCG GCTATATCGT CATGGCAATG    4380
GAAGCAGCCT TAATGATTGC TGGCACCCAC GCAAAGCAGG TCAAGTTACT GGAGATCTTG    4440
GATATGAGCA TTGACAAGGC GGTGATATTT GACGACGAAG ACAGCTTGGT TGAGCTCAAC    4500
CTGACAGCTG ACGTGTCTCG CAACGCCGGC GAAGCAGGTT CAATGACCAT AAGCTTCAAG    4560
ATCGATTCCT GTCTATCGAA GGAGGGTAAC CTATCCCTAT CAGCCAAGGG CCAACTGGCC    4620
CTAACGATAG AAGATGTCAA TCCCAGGACG ACTTCCGCTA GCGACCAGCA CCATCTTCCC    4680
CCGCCAGAAG AGGAACATCC TCATATGAAC CGTGTCAACA TCAATGCTTT CTACCACGAG    4740
CTGGGGTTGA TGGGGTACAA CTACAGTAAG GACTTCCGGC GTCTCCATAA CATGCAACGA    4800
```

FIG. 1H

```
GCAGATCTTC GAGCCAGCGG CACCTTAGAC TTCATTCCTC TGATGGACGA GGGTAATGGC       4860
TGTCCTCTCC TGCTGCATCC TGCATCATTG GACGTCGCCT TCCAGACTGT CATCGGCGCA       4920
TACTCCTCCC CAGGTGATCG GCGTCTACGC TGTCTGTATG TACCCACTCA CGTTGATCGC       4980
ATCACACTTG TCCCATCCCT TTGCCTGGCA ACGGCTGAGT CCGGATGCGA GAAGGTGCC        5040
TTCAATACTA TCAATACGTA CGACAAGGGA GACTACTTGA GCGGTGACAT TGTGGTGTTT       5100
GACGCGGAGC AGACCACCCT GTTCCAGGTT GAAAATATTA CTTTTCACCC                  5160
CCGGATGCTT CAACTGACCA TGCGATGTTT GCCCGATGGA GCTGGGGTCC GTTGACTCCG       5220
GACTCGCTGC TGGATAACCC GGAGTATTGG GCCACCGCGC AGGACAAGGA GGCGATTCCT       5280
```

FIG. 1I

```
ATTATCGAAC GCATCGTCTA CTTCTATATC CGATCGTTCC TCAGTCAGCT TACGCTGGAG   5340
GAGCGCCAGC AGGCAGCCTT CCATTTGCAG AAGCAGATCG AGTGGCTCGA ACAAGTCCTG   5400
GCCAGCGCCA AGGAGGGTCG TCACCTATGG TACGACCCCG GGTGGGAGAA TGATACTGAG   5460
GCCCAGATTG AGCACCTTTG TACTGCTAAC TCCTACCACC CTCATGTTCG CCTGGTTCAG   5520
CGAGTCGGCC AACACCTGCT CCCCACCGTA CGATCGAACG GCAACCCATT CGACCTTCTG   5580
GACCACGATG GGCTCCTGAC GGAGTTCTAT ACCAACACAC TCAGCTTCGG ACCCGCACTA   5640
CACTACGCCC GGGAATTGGT GGCGCAGATC GCCCATCGCT ATCAGTCAAT GGATATTCTG   5700
GAGATTGGAG CAGGGACCGG CGGCGCTACC AAGTACGTGT TGGCCACGCC CCAGCTGGGG   5760
TTCAACAGCT ACACATACAC CGATATCTCC ACCGGATTCT TCGAGCAAGC GCGGGAGCAA   5820
TTTGCCCCCT TCGAGGACCG GATGGTGTTT GAACCCCTCG ATATCCGCCG CAGTCCCGCC   5880
```

FIG. 1J

```
GAGCAGGGCT  TCGAGCCGCA  TGCCTATGAT  CTGATCATTG  CCTCCAATGT  GCTACATGCG  5940

ACACCCGACC  TAGAGAAAAC  CATGGCTCAC  GCCCGCTCTC  TGCTCAAGCC  TGGAGCCAG   6000

ATGGTTATTC  TGGAGATTAC  CCACAAAGAA  CACACACGGC  TCGGGTTTAT  CTTTGGTCTG  6060

TTCGCCGACT  GGTGGGCTGG  GGTGGATGAT  GGTCGCTGCA  CTGAGCCGTT  TGTCTCGTTC  6120

GACCGCTGGG  ATGCGATCCT  AAAGCGTGTC  GGGTTTCCG   GTGTGGACAG  TCGCACCACG  6180

GATCGGGACG  CAAATCTATT  CCCGACCTCT  GTGTTTAGTA  CCCATGCAAT  TGACGCCACC  6240

GTGGAGTACT  TAGACGCGCC  GCTTGCCAGC  AGCGGCACCG  TCAAGGACTC  TTACCCTCCC  6300

TTGGTGGTGG  TAGGAGGGCA  GACCCCCCAA  TCTCAGCGTC  TCCTGAACGA  TATAAAAGCG  6360

ATCATGCCTC  CTCGTCCGCT  CCAGACATAC  AAGCGCCTCG  TGGATTGCT   AGACGCGGAG  6420

GAGCTGCCGA  TGAAGTCCAC  GTTTGTCATG  CTCACGGAGC  TGGACGAGGA  ATTATTCGCC  6480
```

FIG.1K

```
GGGCTCACTG AAGAGACCTT CGAGGCAACC AAGCTGCTGC TCACGTACGC CAGCAATACG    6540
GTCTGGCTGA CAGAAAATGC CTGGGTCCAA CATCCCTCACC AGGCGAGCAC GATCGGCATG   6600
CTACGCTCCA TCCGCCGGGA GCATCCTGAC TTGGGAGTTC ATGTTCTGGA CGTCGACGCG   6660
GTTGAAACCT TCGATGCAAC CTTCCCTGGTT GAACAGGTGC TTCGGCTTGA GGAGCATACG  6720
GATGAGCTGG CCAGTTCAAC TACATGGACT CAAGAACCCG AGGTCTCCTG GTGTAAAGGC   6780
CGCCCGTGGA TTCCTCGTCT GAAGGCGCGAT CTGGCTCGCA ATAACCGAAT GAACTCCTCG  6840
CGCCGTCCCA TATACGAGAT GATCGATTCG TCGCGGGCTC CCGTGGCATT ACAGACGGCT   6900
CGGGATTCAT CATCCTACTT CTTGGAGTCC GCTGAAACCT GGTTTGTGCC TGAGAGTGTT   6960
CAGCAGATGG AAACAAAGAC GATCTATGTC CACTTTAGCT GTCCCCATGC GCTTAGGGTC   7020
```

FIG.1L

```
GGACAGCTCG GGTTTTCTA  TCTTGTGCAG GGTCACGTCC AGGAGGGCAA TCGCGAAGTG   7080
CCCGTCGTGG CCTTAGCAGA GCGTAACGCA TCCATTGTGC ACGTTCGTCC CGATTATATA   7140
TATACTGAGG CAGATAACAA TCTGTCTGAG GGTGGTGGCA GCCTTATGGT AACCGTCCTC   7200
GCCGGGGCGG TGTTGGCGGA GACGGTGATC AGTACCGCCA AGTGCCTGGG GGTAACTGAC   7260
TCAATCCTCG TTCTGAATCC CCCCAGCATA TGTGGGCAGA TGTTGCTCCA TGCTGGTGAA   7320
GAGATCGGTC TTCAAGTTCA TCTGGCCACC ACTTCTGGCA GCTCGCGACA ACAGGAGTTC   7380
GGAGACGCCA AGTCCTGGCT AACATTGCAT GCTCGCGACA CGGACTGGCA GGTTTCTGCT   7440
GTACTGCCCC GGGGTGTCCA GGCTTTAGTC GACTTATCAG CCGACCAGAG CCTGCGACGG   7500
TTGACTCAGA GGATGATGAA AGTTCTGATG CCTGGCTGTG CCCATTACCG CTGTGAAGGT   7560
```

FIG.1M

```
CTGTTCACAG  ACACCGTTTC  CACTGAATTG  CATAGCGGGAT  CGCGGCATCA  AGCTTCACTG   7620

CCCGCCGCAT  ATTGGGAGCA  TGTGGTATCC  TTAGCCCGCC  AGGGACTTCC  TAGTGTCAGC   7680

GAGGGGTGGG  AGTGATGCC   GTGCACTCAA  TTTGCAGCGC  ATGCCGACAA  GACGCGCCCG   7740

GATCTCTCGA  CAGTTATTTC  CTGGCCCCGG  GAGTCGGACG  AGGCTACGCT  TCCTACCAGG   7800

GTTCGCTCCA  TTGACGCTGA  GACCCTCTTT  GCGGCCGACA  AAACATATCT  CCTGGTCGGA   7860

CTGACTGGAG  ATCTTGGACG  ATCACTAGGT  CGTTGGATGG  TCCAGCATGG  GGCCTGCCAC   7920

ATTGTACTTA  CGAGCAGAAA  TCCGCAGGTG  AACCCCAAGT  GGCTGGCGCA  TGTTGAAGAA   7980

CTGGGTGGTC  GAGTCACTGT  TCTTTCCATG  TAAGAGGAGT  CCTTCCTTCT  GCAATTCCTC   8040

CTTATGGATCC  CGACTAACGC  AGCTGGCTTC  AGGGACGTGA  CAAGCCAAAA  CTCAGTGGAA   8100

GCTGGCCCTGG  CTAAACTCAA  GGATCTGCAT  CTGCCACCAG  TGGGGGGTAT  TGCCTTTGGC   8160
```

FIG.1N

```
CCTCTGGTTC TGCAGGATGT GATGCTAAAT AATATGGAAC TGCCAATGAT GGAGATGGTG   8220
CTCAACCCCA AGTCGAAGG  CGTCCGCATC CTGCACGAGA AGTTCTCCGA TCCGACCAGT   8280
AGCAACCCTC TCGACTTCTT CGTGATGTTC TCCTCGATTG TGGCCGTCAT GGGCAACCCG   8340
GGTCAGGCTA ACTACAGTGC GGCTAACTGC TACCTTCAAG CGCTGGGCGCA GCAGCGAGTT   8400
GCATCCGGAT TAGCAGTACG TTTTCACTCC ATCCTTTGCT AAACACTCCT ATGGGCCTTT   8460
ACTAAACCGG GCAGGCGTCC ACCATCGACA TCGGTGCCGT GTACGGGCGTT GGGTTCGTCA   8520
CTCGGGGCGGA GCTGGAGGAG GACTTTAATG CAATTCGGTT CATGTTCGAT TCGGTTGAGG   8580
AACATGAACT GCATACACTG TTTGCTGAGG CAGTGGTGGC CGGTCGACGA GCCGTGCACC   8640
AGCAAGAGCA GCAGCGGAAG TTCGCGACAG TGCTCGACAT GGCTGATCTG GAACTGACAA   8700
```

FIG. 10

```
CCGGAATTCC GCCCCTGGAT CCAGCCCTCA AAGATCGGAT CACCTTCTTC GACGACCCCC    8760
GCATAGGCAA CTTAAAAATT CCGGAGTACC GAGGGGCCAA AGCAGGCGAA GGGGCAGCCG    8820
GCTCCAAGGG CTCGGTCAAA GAACAGCTCT TGCAGGCGAC GAACCTGGAC CAGGTCCGTC    8880
AGATCGTCAT CGGTAAGTTG AGCGAATCCG GGGAATATTC TCCCCTTCCT CACTCAGCGG    8940
ACTGGAGATT AACCGCTTCT TTTCCTTTGG CAGATGGACT CTCCGCGAAG CTGCAGGTGA    9000
CCCTGCAGAT CCCCGATGGG GAAAGCGTGC ATCCCACCAT CCCACTAATC GATCAGGGGG    9060
TGGACTCTCT GGGCGCGGTC ACCGTGGGAA CCTGGTCTC CAAGCAGCTG TACCTTGATT    9120
TGCCACTCCT GAAAGTGCTT GGGGGTGCTT CGATCACCGA TCTCGCTAAT GAGGCTGCTG    9180
CGCGATTGCC ACCTAGCTCC ATTCCCCTCG TGCCAGCCAC CGACGGGGGT GCAGAGAGCA    9240
CTGACAATAC TTCCGAGAAT GAAGTTTCGG GACGCGAGGA TACTGACCTT AGTGCCGCCG    9300
```

FIG. 1P

| | | | | |
|---|---|---|---|---|
| CCACCATCAC | TGAGCCCTCG | TCTGCCGACG | AAGACGATAC | GGAGCCGGGC | GACGAGGACG | 9360 |
| TCCCGCGTTC | CCACCATCCA | CTGTCTCTCG | GGCAAGAATA | CTCCTGGAGA | ATCCAGCAGG | 9420 |
| GAGCCGAAGA | CCCCACCGTC | TTTAACAACA | CCATTGGTAT | GTTCATGAAG | GGCTCTATTG | 9480 |
| ACCTTAAACG | GCTGTACAAG | GCGTTGAGAG | CGGTCTTGCG | CCGCCACGAG | ATCTTCCGCA | 9540 |
| CGGGGTTTGC | CAACGTGGAT | GAGAACGGGA | TGGCCCAGCT | GGTGTTTGGT | CAAACCAAAA | 9600 |
| ACAAAGTCCA | GACCATCCAA | GTGTCTGACC | GAGCCGGGCG | CGAAGAGGGC | TACCGACAAC | 9660 |
| TGGTGCAGAC | ACGGTATAAC | CCTGCCCGCA | GAGACACCTT | GCGGCTGGTG | GACTTCTTCT | 9720 |
| GGGGCCAGGA | CGACCATCTG | CTGGTTGTGG | CTTACCACCG | ACTCGTCGGG | GATGGATCTA | 9780 |
| CTACAGAGAA | CATCTTCCGT | GAAGCGGGCC | AGCTCTACGA | CGGCACGTCG | CTAAGTCCAC | 9840 |

FIG. 1Q

```
ATGTCCCTCA GTTTGCGGAC CTGGGGGCAC GGCAACGCGC AATGCTCGAG GATGGAGAA   9900
TGGAGGAGGA TCTCGCGTAC TGGAAGAAAA TGCATTACCG ACCGTCCTCA ATTCCAGTGC  9960
TCCCACTGAT GCGGCCCCTG GTAGGTAACA GTAGCAGGTC CGATACTCCA AATTCCAGC  10020
ACTGTGGACC CTGGCAGCAG CACGAAGCCG TGGCGCGACT TGATCCGATG GTGGCCTTCC  10080
GCATCAAGGA GCGCAGTCGC AAGCACAAGG CGACGCCGAT GCAGTTCTAT CTGGGGGCGT  10140
ATCAGGTGCT GTTGGCGCGC CTCACCGACA GCACCGATCT CACCGTGGGC CTCGCCGACA  10200
CCAACCGTGC GACTGTCGAC GAGATGGCGG CCATGGGGTT CTTCGCCAAC CTCCTTCCCC  10260
TGCGCTTCCG GGATTCCGCC CCCCATATAA CGTTGGCGGA GCACCTTATC GCCACCCGTG  10320
ACCTGGTGCG TGAGGCCTTG CAGCACGCCC GCGTGCCCTA CGGCGTCCTC CTCGATCAAC  10380
```

FIG. 1R

```
TGGGGCTGGA GGTCCCGGTC CCGACCAGCA ATCAACCTGC GCCTTTGTTC CAGGCCGTCT   10440
TCGATTACAA GCAGGGCCAG GCGGAAAGTG GAACGATTGG GGGTGCCAAG ATAACCGAGG   10500
TGATTGCCAC GCGCGGAGCGC ACCCCTTACG ATGTCGTGCT GGAGATGTCG GATGATCCCA   10560
CCAAGGATCC GCTGCTCACG GCCAAGTTAC AGAGTTCCCG CTACGAGGCT CACCACCCTC   10620
AAGCCTTCTT GGAGAGCTAC ATGTCCCTTC TCTCTATGTT CTCGATGAAT CCCGCCCTGA   10680
AGCTGGCATG ATGGCGCAAA CATAGAACAT GATAGCGCAG CAGGGACGAT GTAGATAGAG   10740
CTTTGCTTCT GCGGGTGGAT CTATAATATA GTATATATAA ATATGGTGAG CCGAACGAAG   10800
AGGGGGGAAT GCCACAATTA TTTACTGTTT TGCGCCCGTAC ACGAGGAGAA GACGTCCAGA   10860
ACAACATAAA TATATCACTC TAGTGAGACA CCATATATTC GGAGAGACTA TAAAAATATA   10920
CATCTACTCC AATGTCTGGG CCGTCACACA CAGCTTACGA AAACGATTAA TGACCTCCAA   10980
```

FIG.1S

```
CACGTCGCGC  GGTCGATTGG  GAAACTGATG  CTGCCCAGCA  AACTCCAATA  CCTGCGCCTC   11040
TCGGGGGAG   AAATGGCGCG  CCACCAGCAT  CTTCGATCCT  GCGAGCGCAA  AATCATCGCG   11100
ACCCTGCAGA  TGTAATGTCG  GTATCCGAAT  GACCAGTTCC  TCCTGCCACT  CGGTATCTTT   11160
GCTGTCGTTG  TCGTCGTCAT  GGTTCTTCAT  CATTCGTTCC  TCATATACTG  GCTTGCCTCG   11220
TCTTGATACC  AGGGACAGAT  CAACAGGCA   GAGCAAGGTC  GGGGCAACCA  GGGCAGTGA    11280
CCCATCTGCT  GCTGCCAGAG  GTCACCAGGG  GTCACCAGGG  CACCTTCGGA  GAAACCGATA   11340
GCACCCACGA  TAGGGATGTG  GGGGTGTTGA  GTCTGCCAGT  CGACAATGGT  GCGGCCGATG   11400
GGGTCGTGGA  CGGCGGCGAG  GCGTTCGCTC  ACGGAGGGTC  CATTATGATT  GTTGTCGCTG   11460
CTGCTTTCAA  ACCAGGAGTA  ATATGGCCCT  AGGTCGGGCA  AGACGGGGAG  AATCCCAGGC   11520

CCTGCAGAGG  AAGGGAACGG  AGCTGTCACG  TAGACGAATT  C                         11561
```

FIG. 1T

```
              10         20         30         40         50
         1234567890 1234567890 1234567890 1234567890 1234567890
         MAQSMYPNEP IVVVGSGCRF PGDANTPSKL WELLQHPRDV QSRIPKERFD    50

VDTFYHPDGK HHGRTNAPYA YVLQDDLGAF DAAFFNIQAG EAESMDPQHR   100

LLLETVYEAV TNAGMRIQDL QGTSTAVYVG VMIHDYETVS TRDLESIPTY   150

SATGVAVSVA SNRISYFFDW HGPSMTTDTA CSSSLVAVHL AVQQLRTGQS   200

SMAIAAGANL ILGPMTFVLE SKLSMLSPSG RSRMWDAGAD GYARGEAVCS   250

VVLKTLSQAL RDGDTTECVI RETGVNQDGR TIGTIMPKHS AQEALIKATY   300

AQAGLDITKA EDRCQFFEAH GTGTPAGDPQ EAEAIATAFF GHEQVAPGGG   350

NERAPLFVGS AKTVVGHTEG TAGLAGLMKA SFAVRHGVIP PNLLFIKISP   400

RVAPFYKNLR IPTEATQWPA LPPGQPRRAS VNSFGFGGIN AHAIEEYME    450

PEQNQLRVSN NEDCPPMTGV LSLPLVLSAK SQRSLKIMME EMLQFLQSHP   500

EIHLHDETWS LLRKRSVLPF RRAIVGHSHE TEAAALEDAI EDGIVSSDIT   550

TEVRGQPSVL GIFTGQGAQW PGMLKNLIEA SPVYRNIVRE LDDSLQSLPE   600

KYRPSWTLLD QFMLEGEASN VQYATFSQPL CCAVQIVLVR LLEAARIRFT   650

AVVGHSSGEI ACAFAAGLIS ASLAIRIAYL RGVVSAGGAR GTPGAMLAAG   700

MSFEEAQEIC ELDAFEGRIC VAASNSPDSV TFSGDANAID HLKGMLEDES   750

TFARLLKVDT AYHSHHMLPC ADPYMQALEE CGCAVADAGS PAGSVPWYSS   800

VDAENRQMAA RDVTAKYWKD NLVSPVLFSH AVQRAVVIHK ALDIGIEVGC   850

HPALKSPCVA TIKDVLSGVD LAYTGCLERG KNDLDSFSRA LAYLWERFGA   900

SSFDADEFMR AVAPDRPQMS VSKLLPAYPW DRSRRYWVES RATRHHLPGP   950
```

FIG.2A

```
           10         20         30         40         50
    1234567890 1234567890 1234567890 1234567890 1234567890
    KPHLLLGKLS EYSTPLSFQW LNFVRPRDIE WLDGHALQGQ TVFPAAGYTV   1000

MAMEAALMIA GTHAKQVKLL ETLDMSIDKA VIFDDEDSLV ELNLTADVSR   1050

NAGEAGSMTI SFKIDSCLSK EGNLSLSAKG QLALTIEDVN PRTTSASDQH   1100

HLPPPEEEHP HMNRVNINAF YHELGLMGYN YSKDFRRLHN MQRADLRASG   1150

TLDFIPLMDE GNGCPLLLHP ASLDVAFQTV IGAYSSPGDR RLRCLYVPTH   1200

VDRITLVPSL CLATAESGCE KVAFNTTNTY DKGDYLSGDI VVFDAEQTTL   1250

FQVENTTFKP FSPPDASTDH AMFARWSWGP LTPDSLLDNP EYWATAQDKE   1300

AIPIIERIVY FYIRSFLSQL TLEERQQAAF HLQKQIEWLE QVLASAKEGR   1350

HLWYDPGWEN DTEAQIEHLC TANSYHPHVR LVQRVGQHLL PTVRSNGNPF   1400

DLLDHDGLLT EFYTNTLSFG PALHYARELV AQIAHRYQSM DILEIGAGTG   1450

GATKYVLATP QLGFNSYTYT DISTGFFEQA REQFAPFEDR MVFEPLDIRR   1500

SPAEQGFEPH AYDLIIASWV LHATPDLEKT MAHARSLLKP GGQMVILETT   1550

HKEHTRLGFI FGLFADWWAG VDDGRCTEPF VSFDRWDAIL KRVGFSGVDS   1600

RTTDRDANLF PTSVFSTHAI DATVEYLDAP LASSGTVKDS YPPLVVVGGQ   1650

TPQSQRLLND IKAIMPPRPL QTYKRLVDLL DAEELPMKST FVMLTELDEE   1700

LFAGLTEETF EATKLLLTYA SNTVWLTENA WVQHPHQAST IGMLRSIRRE   1750

HPDLGVHVLD VDAVETFDAT FLVEQVLRLE EHTDELASST TWTQEPEVSW   1800

CKGRPWIPRL MRDLARNNRM NSSRRPIYEM IDSSRAPVAL QTARDSSSYF   1850

LESAETWFVP ESVQQMETKT IYVHFSCPHA LRVGQLGFFY LVQGHVQEGN   1900

REVPVVALAE RNASIVHVRP DYTYTEADNN LSEGGGSLMV TVLAAAVLAE   1950
```

FIG.2B

```
            10         20         30         40         50
     1234567890 1234567890 1234567890 1234567890 1234567890
     TVISTAMCLG VIDSILVLNP PSICGQMLLH AGEEIGLQVH LATTSGNRSS    2000

VSAGDAKSAL TLHARDTDWH LRRVLPRGVQ ALVDLSADQS CEGLTQRMMK    2050

VIMPGCAHYR AADLFTDTVS TELHSGSRHQ ASLPAAYWEH VVSLARQGLP    2100

SVSEGWEVMP CTQFAAHADK TRPDLSTVIS WPRESDEATL PTRVRSIDAE    2150

TLFAADKTYL LVGLTGDLGR SLGRWWVQHG ACHIVLTSRN PQVNPKWLAH    2200

VEELGGRVTV LSMDVTSQNS VEAGLAKLKD LHLPPVGGIA FGPLVLQQVM    2250

LNNMELPMME MVLNPKVEGV RILHEKFSDP TSSNPLDFFV MFSSIVAVMG    2300

NPGQANYSAA NCYLQALAQQ RVASGLAAST IDIGAVYGVG FVTRAELEED    2350

FNAIRFMFDS VEEHELHTLF AEAVVAGRRA VHQQEQQRKF ATVLDMADLE    2400

LTTGIPPLDP ALKDRITFFD DPRIGNLKIP EYRGAKAGEG AAGSKGSVKE    2450

QLLQATNLDQ VRQIVIDGLS AKLQVTLQIP DGESVHPTIP LIDQGVDSLG    2500

AVTVGTWFSK QLYLDLPLLK VLGGASITDL ANEAAARLPP SSIPLVAATD    2550

GGAESTDNTS ENEVSGREDT DLSAAATTTE PSSADEDDTE PGDEDVPRSH    2600

HPLSLGQEYS WRIQQGAEDP TVFNNTIGMF MKGSIDLKRL YKALRAVLRR    2650

HEIFRTGFAN VDENGMAQLV FGQTKNKVQT IQVSDRAGAE EGYRQLVQTR    2700

YNPAAGDTLR LVDFFWGQDD HLLVVAYHRL VGDGSTTENI FVEAGQLYDG    2750

TSLSPHVPQF ADLAARQRAM LEDGRMEEDL AYWKKMHYRP SSIPVLPLMR    2800

PLVGNSSRSD TRNFQHCGPW QQHEAVARLD RMVAFRIKER SRKHKATPMQ    2850

FYLAAYQVLL ARLTDSTDLT VGLADINRAT VDEMAAMGFF ANLLPLRFRD    2900

FRPHITFGEH LIATRDLVRE ALQHARVPYG VLLDQLGLEV PVPTSNQPAP    2950

LFQAVFDYKQ GQAESGTIGG AKITEVIATR ERTPYDVVLE MSDDPTKDPL    3000

LTAKLQSSRY EAHHPQAFLE SYMSLLSMFS MNPALKLA                 3038
```

FIG.2C

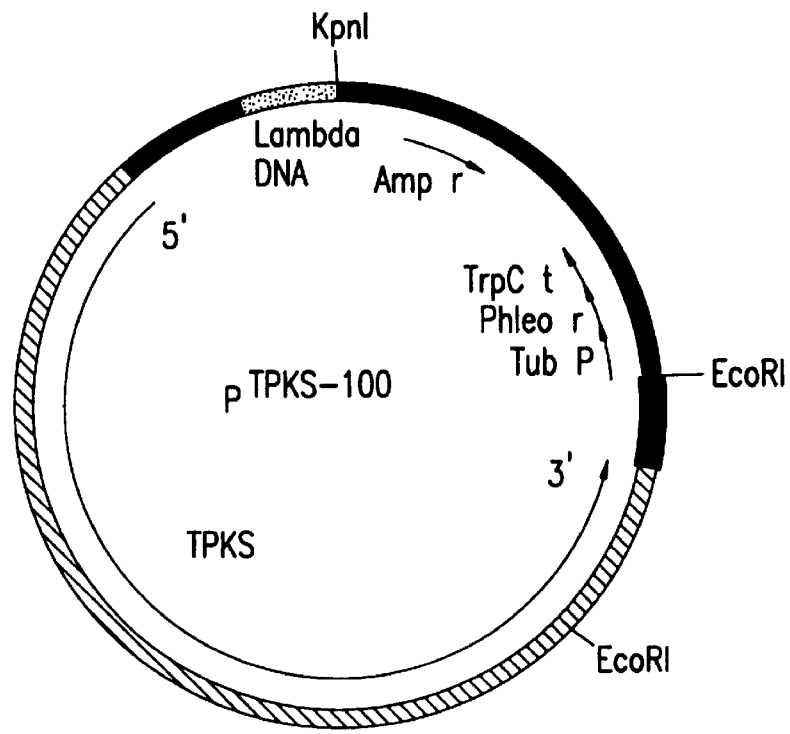
ASPERGILLUS TERREUS DNA:
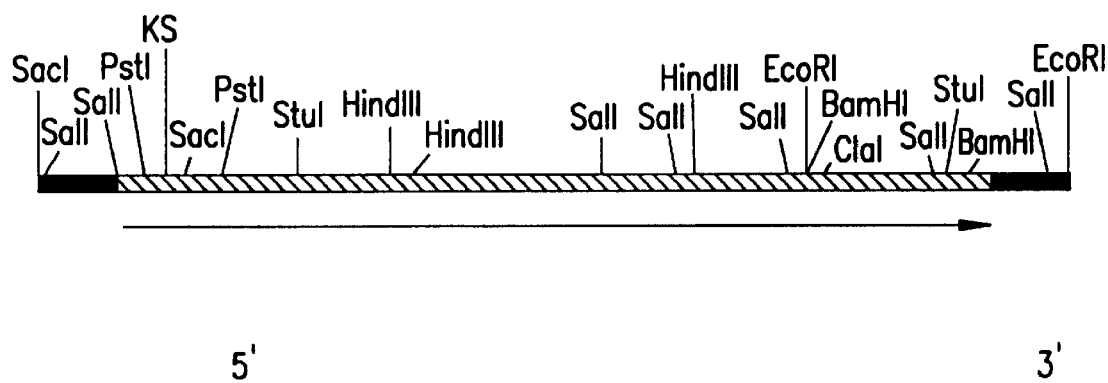
FIG.3

KETO ACYLSYNTHASE ALIGNMENT

```
FAS_RATF   (130-229)   YSMVGCQRAM MANRLSFFFD FKGPSIALDT ACSSSLLALQ NAYQAIRSGE
TRIOL PKS  (150-249)   YSATGVAVSV ASNRISYFFD WHGPSMTIDT ACSSSLVAVH LAVQQLRTGQ
MSAS_PENPA (173-272)   WMGIGTAYCG VPNRISYHLN LMGPSTAVDA ACASSLVAIH HGVQAIRLGE

Consensus              .........G ........NR.S..... ...GPS...D. AC.SSL.A.. ...Q..R.G.
```

ACETYL/MALONYL TRANSFERASE ALIGNMENT

```
MSAS_PENPA (621-671)   SDRVQILTYV MQIGLSALLQ SNGITPQAVI GHSVGEIAAS VVAGALSPAE
FAS_RATF   (553-603)   F-V-SL-TA  IQIALIDLLT SMGLKPDGII GHSLGEVACG YADCCLSQRE
TRIOL PKS  (626-676)   F---SQPLCCA VQIVLVRLLE AARIRFTAVV GHSSGEIACA FAAGLISASL

Consensus              F........ ...QI.L..LL ......... GHS.GE.A.. ...G..S...
```

DEHYDRATASE ALIGNMENT

```
MSAS_PENPA (943-982)   YTTRLDNDTK PFPGSHPLHC TEIVPAAGLI NTFLKGTGCQ
FAS_RATF   (863-902)   NIDASSESSD HYLVDHCIDG RVLFPGTGYL YLVWK-TLAR S
TRIOL PKS  (970-1010)  WLNFVRPRDI EWLDGHALQG QTVFPAAGYI VMAMEAALMI A

Consensus              .......... ......H..G ....P.G... ..........
```

FIG.5

ENOYL REDUCTASE ALIGNMENT

```
TRIOL PKS (1903-1950)   VPVVALAERN ASIVHVRPDY IYTEADNNLS EGGGSLMVTV LAAAVLAE
FAS_RATF (1642-1691)    VPVVYTTAYY SLVVRGRIQH GETVLIHSGS GGVGQAAISI ALSLGCRVFT
SU4 ER                  VPIAYTTAHY ALHDLAGLRA GQSVLIHAAA GGVGMAAVAL ARRAG-LAEV

Consensus               VP.......... .......... .......G.G .......... ..........
```

KETO REDUCTASE ALIGNMENT

```
TRIOL PKS (2141-2196)   PTRVRSIDAE TLFAADKTYL LVGLTGDLGR SLGRWMVQHG ACHIVLTSRN
MSAS_PENPA (1398-1451)  LP-ASEG-PR LLPRPEGTYL ITGGLGVLGL EVADFLVEKG ARRLLLISRR
FAS_RATF (1864-1921)    PTLISAI-SK TFCPEHKSYI ITGGLGGFGL ELARWLVLRG AQRLVLTSRS

Consensus               .......... .......Y .G.G.G .......... .V.G A....L.SR.
```

ACYL CARRIER PROTEIN ALIGNMENT

```
TRIOL PKS (2461-2548)   VRQIVIDGLS AKLQVTLQIP DGESVHPTIP LIDQGVDSLG AVTVGTWFSK
FAS_RATF (2114-2201)    GDGEAQRDLV KAVAHILGIR DLAGINLDSS LADLGLDSLM GVEVRQILER
MSAS_PENPA (1697-1758)  -KAYLDEKIR GCVAKVLQMT A-EDVDSKAA LADLGVDSVM TVTLRRQLQ-

Consensus               .......... .......L.. .......... L.D.G.DS.. V.........
```

FIG.6

ALCOHOL
DEHYDROGENASE  S T C A V F G L G G V G L S V I M G C K A A
               β [TTTTT]  α [██████] 14aa R 22aa K

RAT FAS-ER     T V L I H S G S G G V G Q A A I S I A L S L
               β [TTTTT]  α [███░░░] 14aa R 23aa K

TPKS-ER        Y I Y T E A D N N L S E G G G S L M V T V L
               β [TTTTTTT]  β [░░░░░] 20aa K

TPKS-KR        T Y L L V G L T G D L G R S L G R W M V Q H
               β [TTTTTT]  β [░░░░░] 20aa K

MSAS-KR        T Y L I T G G L G V L G L E V A D F L V E K
               β [TTTT]  α [██████░░] 14aa R 20aa R

RAT FAS KR     S Y I I T G G L G G F G L E L A R W L V L R
               β [TTTTTT]  α [██████] 14aa R 20aa R

FIG.7

| Potential SAM Binding Region in Methyl Transferase | |
|---|---|
| Consensus | △△△D/E△GXGXGX△XXX△△∧/P |
| TPKS (1444) | I L E I GAGTGG A TKY V L P |

△ = hydrophobic A.A.
X = any A.A.
∧ = charged A.A.

FIG. 8

DNA ENCODING TRIOL POLYKETIDE SYNTHASE

CROSS-RELATED TO OTHER APPLICATIONS

This is a continuation of U.S. Ser. No. 08/148,132 filed. Nov. 2, 1993, a 371 of PCT/US94/12423 filed Oct. 28, 1994, which is now abandoned.

BACKGROUND OF THE INVENTION

Hyperchlosterolemia is known to be one of the prime risk factors for ischemic cardiovascular diseases such as arteriosclerosis. Cholesterol and other lipids are transported in body fluids by lipoproteins of varying density. The two lipoproteins carrying the majority of cholesterol in the blood are low-density lipoproteins (LDL) and high-density lipoproteins (HDL). The role of LDL is to transport cholesterol to peripheral cells outside the liver. LDL-receptors on a cell plasma membrane bind LDL and allow entry of cholesterol into the cell. HDL may scavenge cholesterol in the tissues for transport to the liver and eventual catabolism. LDL levels are positively correlated with the risk of coronary artery disease while HDL levels are negatively related, and the ratio of LDL-cholesterol to HDL-cholesterol has been reported to be the best predictor of coronary artery disease. Thus substances which effectuate mechanisms for lowering LDL-cholesterol may serve as effective antihypercholesterolemic agents.

Mevacor® (lovastatin; mevinolin) and ZOCOR® (simvastatin), now commercially available, are two of a group of very active antihypercholesterolemic agents that function by inhibiting the enzyme HMG-CoA reductase. Lovastatin and related compounds inhibit cholesterol synthesis by inhibiting the rate-limiting step in cellular cholesterol biosynthesis, namely the conversion of hydroxymethyl-glutarylcoenzyme A (HMG-CoA) into mevalonate by HMG-CoA reductase [3.7-9.12]. HMG-CoA reductase inhibitors act through cellular homeostatic mechanisms to increase LDL receptors with a consequent reduction in LDL-cholesterol and a resultant therapeutic antihypercholesterolemic effect. The HMG-CoA reductase inhibitors within this invention include, but are not limited to compactin (ML-236B), lovastatin, simvastatin, pravastatin, fluvastatin and mevastatin.

Many HMG-CoA reductase inhibitors are synthesized by microorganisms. The general biosynthetic pathway of the HMG-CoA reductase inhibitors of the present invention has been outlined by Moore et al., who showed that the biosynthesis of mevinolin (lovastatin) by *Aspergillus terreus* ATCC 20542 proceeds from acetate via a polyketide pathway (R. N. Moore et al., Biosynthesis of the hypocholesterolemic agent mevinolin by *Aspergillus terreus*. Determination of the origin of carbon, hydrogen, and oxygen atoms by $^{13}$C NMR and mass spectrometry. *J. Amer. Chem. Soc.*, 1985, 107: 3694–3701). Endo and his coworkers demonstrated that similar biosynthetic pathways existed in *Pencillium citrinum* NRRL 8082 and *Monascus ruber* M-4681 (A. Y. Endo et al., Biosynthesis of ML-236B (compactin) and monacolin K., 1985, *J. Antibiot.*, 38: 444–448).

The recent commercial introduction of HMG-CoA reductase inhibitors has provided a need for high yielding processes for their production. Methods of improving process yield include, but are not limited to scaling up the process, improving the culture medium or, simplifying the isolation train. The present invention focuses on a method of increasing process yield wherein the increase in productivity is due to the use of a microorganism that produces increased levels of HMG-CoA reductase inhibitor.

It may be desirable to increase the biosynthesis of HMG-CoA reductase inhibitors at the level of gene expression. Such increases could be achieved by increasing the concentration in an HMG-CoA reductase inhibitor-producing microorganism of one or more of the enzymes or enzymatic activities in the biosynthetic pathway of the HMG-CoA reductase inhibitor. It may be particularly desirable to increase the concentration of a rate-limiting biosynthetic activity.

Triol polyketide synthase (TPKS) is a multifunctional protein with at least four activities as evidenced by the product of the enzymatic activity (Moore, supra). TPKS is believed to be the rate-limiting enzymatic activity(ies) in the biosynthesis of the HMG-CoA reductase inhibitor compounds.

The present invention identifies a DNA encoding triol polyketide synthase (TPKS) from *Aspergillus terreus*. The DNA encoding the TPKS of the present invention has been isolated, purified and sequenced. Complementary DNA (cDNA) and genomic DNA sequences corresponding to TPKS have been prepared. The TPKS cDNA of the present invention may be used to increase the production of HMG-CoA reductase inhibitors by HMG-CoA reductase inhibitor-producing microorganisms. The TPKS cDNA of the present invention may also be used to produce purified TPKS.

SUMMARY OF THE INVENTION

DNA encoding the full-length form of triol polyketide synthase (TPKS) is identified. The DNA is sequenced and cloned into expression vectors. Cells transformed with the expression vectors produce increased levels of TPKS and increased levels of HMG-CoA reductase inhibitors. The DNA is useful to produce recombinant full-length TPKS. The DNA may be used to isolate and identify homologues of TPKS present in organisms that are capable of producing polyketides, particularly microorganisms that are capable of producing HMG-CoA reductase inhibitors.

BRIEF DESCRIPTION OF THE DRAWINGS

FIGS. 1A–1T are the nucleotide sequence of triol polyketide synthase.

FIGS. 2A–2C are the predicted amino acid sequence of triol polyketide synthase.

FIG. 3 shows pTPKS100.

FIG. 5 shows the alignments of keto acyl synthase, acetyl/malonyl transferase and dehydratase carried out on regions of TPKS, rat fatty acid synthase (FAS) and *P. patulum* 6MSAS.

FIG. 6 shows the alignments of enoyl reductase, keto reductase and acyl carrier protein carried out on regions of TPKS.

FIG. 7 is a Chou-Fasman secondary structure prediction of pyridine nucleotide binding regions of TPKS and related proteins.

FIG. 8 shows the S-adenosylmethionine binding regions of a variety of prokaryotic and eukaryotic methyl transferases.

DETAILED DESCRIPTION OF THE INVENTION

Figure 4:
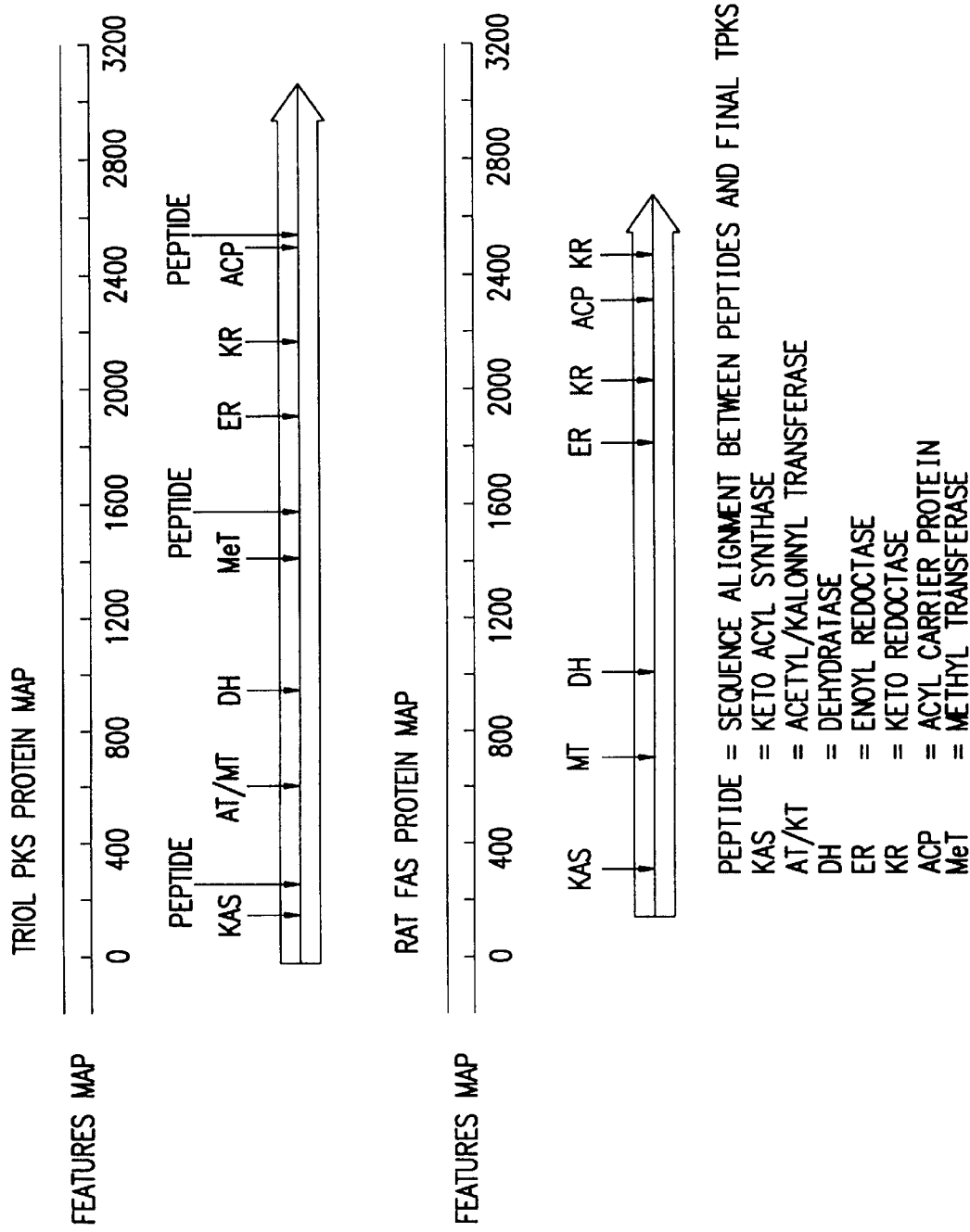
FIG. 4 is a graphic view of the open reading frame of the TPKS protein and the overall placement of the TPKS peptides and PKS activities established by alignments generated by the Intelligenetics GeneWorks program.
Figure 9:
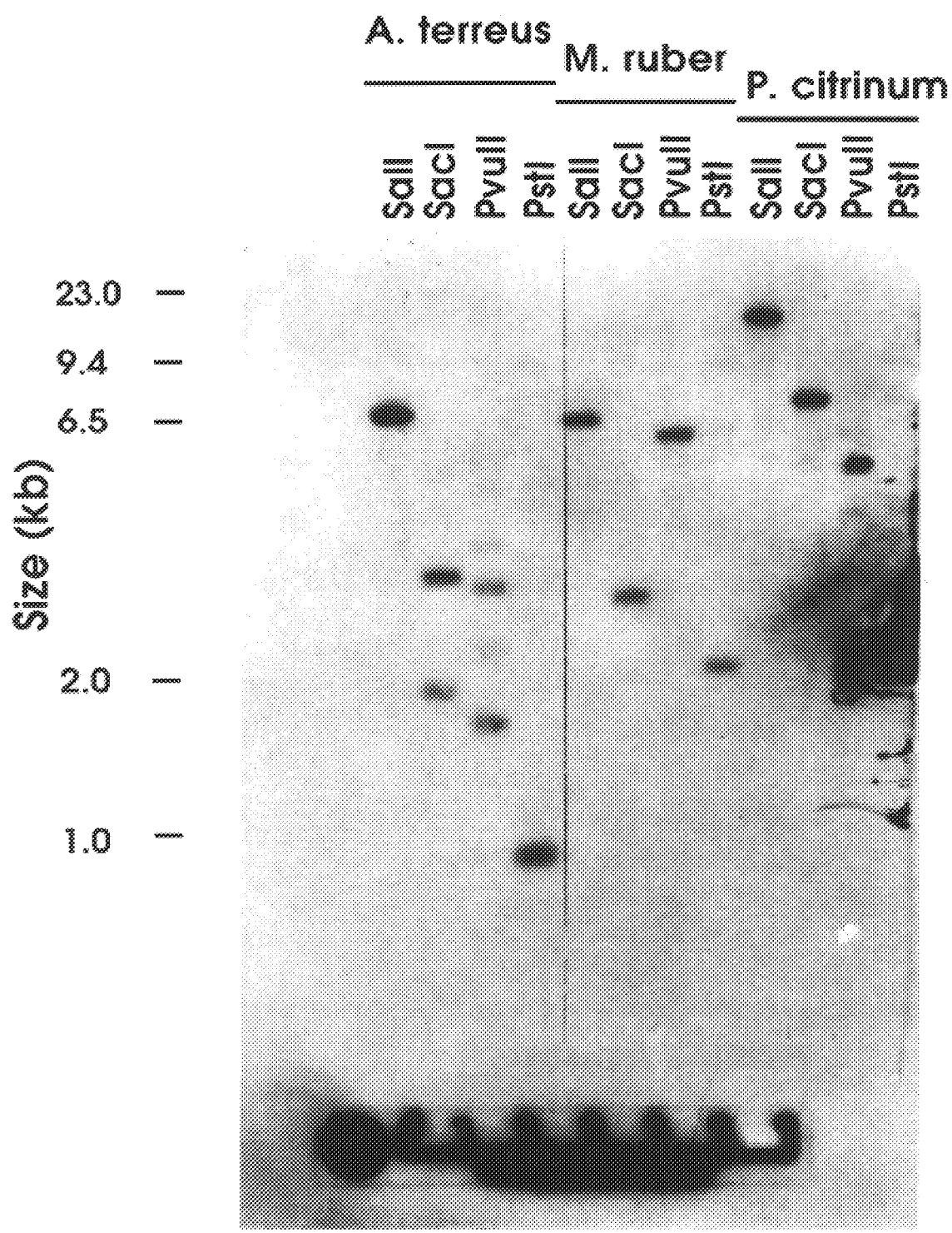
FIG. 9 is a Southern blot showing the homology of ketoacylsynthase of the TPKS of *A. terreus* to *M. ruber* and *P. citrinum*.

The present invention relates to a DNA molecule encoding triol polyketide synthase (TPKS) which is isolated from TPKS-producing cells. Cells capable of producing TPKS include, but are not limited to, strains of *Aspergillus terreus, Monascus ruber, Penicillum citrinum, Penicillum brevicompactum, Hypomyces chrysospermus,* Paecilomyces sp M2016, Eupenicillium sp. MM603, *Trichoderma longibrachiatum* M6735 and *Trichoderma pseudokoningii* M6828.

TPKS, as used herein, refers to enzymatic activities that convert acetate precursors and S-adenosyl methionine to an intermediate in the triol biosynthetic pathway. This intermediate is further modified to produce a triol nonaketide. Polyketide synthases from bacteria and fungi employ common enzymatic functions to synthesize polyketides from two carbon units (for a review, see D. A. Hopwood and D. H. Sherman, 1990, "Comparison to fatty acid biosynthesis", *Ann. Rev. Genet.,* 24: 37–66).

Polyketides are an important class of natural products because of their structural diversity and because many have antibiotic or other pharmaceutical activities. Most of the economically important polyketides are produced by fungi or actinomycetes.

Polyketide biosynthesis is similar to that of fatty acid biosynthesis in that it involves the sequential condensation of carboxylate units. Unlike fatty acids, which are built from acetate units, polyketides may be built from acetate, propionate, or butyrate units. Additionally, some or all of the β-keto groups added at each cycle of condensation during polyketide biosynthesis are left unreduced, or are reduced only to hydroxyl or enoyl functionalities. This variation in building units and the variation in modification of the beta-keto groups results in a tremendous variety of products as well as difficulty in comparing biosynthetic genes from different pathways.

*Aspergillus terreus* is a filamentous soil fungus; different strains of *A. terreus* produce a variety of polyketides (Springer, J. et al., 1979, terretonin, a toxic compound from *Aspergillus terreus, J. Org. Chem.,* Vol. 44, No. 26, 4852–4854). Lovastatin is a polyketide produced by certain strains of *A. terreus* (Moore, supra). In addition to lovastatin and related metabolites such as triol or monacolin J, other polyketides found in *A. terreus* include sulochrin and related structures (Curtis, R. G. et al.,1964, "The biosynthesis of phenols", *J. Biochem.,* 90: 43–51) derived from emodin (Fujii, I., et al., 1982, "Partial purification and some properties of emodin-o-methyltransferase from (+)-geodin producing strain of *Aspergillus terreus". Chem. Pharm. Bull.,* 30(6):2283–2286); terreic acid (Sheehan, J. C. et al., 1958, *J. Am. Chem. Soc.,* 80: 5536); patulin (D. M. Wilson, 1976, "Adv. Chem. Ser. No. 149") and citrinin (Sankawa, U. et al., 1983, "Biosynthesis of citrinin in *Aspergillus terreus", Tetrahedron,* 39(21): 3583–3591). Presumably each of these products is made by a specific PKS encoded by a specific and distinct PKS gene(s), thus increasing the difficulty in cloning the triol PKS.

The structure and activity of lovastatin was reported by A. Alberts et al., (*Proc. Natl. Acad. Sci. U.S.A.,* 1980, 77: 3957–3961). Lovastatin is a reduced molecule consisting of a methylbutyryl group joined by an ester linkage to a nonaketide having a conjugated decene ring system.

Moore et al., (supra) described lovastatin biosynthesis. Proton and $^{13}C$ NMR studies of in vivo labeled lovastatin showed that all the carbons are derived from acetate except in the methyl groups at positions 6 and 2', which were derived from methionine. The triol molecule is composed of nine acetate units. The side-chain is composed of two acetate units. Esterification of triol and the butyrate side chain occurs enzymatically (Kimura, supra). The methyl butyrate side chain is presumably synthesized by a separate PKS. Lovastatin is first synthesized as a highly reduced precursor longer than 9 acetate units which undergoes reoxidation, including oxidative cleavage of a carbon-carbon bond.

Limited information is available for compactin biosynthesis. The most likely pathway would be nearly identical to that of lovastatin biosynthesis in *M. ruber* and *A. terreus,* except that methylation does not occur at the 6 position on the diene ring system.

Polyketide synthases (PKS) and fatty acid synthases (FAS) are classified by functional types. Type II enzymes, typical of bacteria and plants, have a separate polypeptide for each enzymatic activity. Type I enzymes, found in animals, bacteria and fungi, consist of large polypeptides with multiple activities or functional domains. Regions of amino acid sequence similarity have been identified in these genes: domains for ketoacyl synthase, acetyl/malonyl transferase, β-keto reductase, enoyl reductase, dehydratase and acyl carrier protein. The identification of these domains is considered evidence of the resulting enzymatic activity in light of the difficulty in obtaining functional Type I PKS in vitro (Sherman, supra).

Any of a variety of procedures may be used to molecularly clone the TPKS genomic DNA or complementary DNA (cDNA). These methods include but are not limited to, direct functional expression of the TPKS gene in an appropriate host following the construction of a TPKS-containing genomic DNA or cDNA library in an appropriate expression vector system. The preferred method consists of screening a TPKS-containing cDNA expression library constructed in a bacteriophage or vector with an antibody directed against the purified TPKS protein. The antibody is obtained by standard methods (Deutscher, M. (ed), 1990, *Methods in Enzymology, Vol.* 182) by isolating purified TPKS protein from HMG-CoA reductase inhibitor-producing cells, inoculating an appropriate host, such as a rabbit, with the purified protein and, after several boosts, collecting immune sera. Antibody collected from the animal is used to screen the cDNA expression library and cDNA clones expressing TPKS epitopes recognized by the antisera are selected. The positive clones are further purified, labeled and used to probe TPKS-containing genomic or cDNA libraries to identify related TPKS containing DNA. Standard restriction analysis of the related clones can be used to create a restriction map of the region and sequence analysis of the genomic and cDNA clones can be used to define a structural map and the open reading frame of the gene, respectively.

Another method of cloning TPKS involves screening a TPKS-containing cDNA library constructed in a bacteriophage or plasmid shuttle vector with a labelled oligonucleotide probe designed from the amino acid sequence of TPKS. The method may consist of screening an TPKS-containing cDNA library constructed in a bacteriophage or plasmid shuttle vector with a partial cDNA encoding the TPKS subunits. This partial cDNA is obtained by the specific PCR amplification of TPKS DNA fragments through the design of degenerate oligonucleotide primers from the amino acid sequence of the purified TPKS subunits.

It is readily apparent to those skilled in the art that other types of libraries, as well as libraries constructed from other cells or cell types, may be useful for isolating TPKS-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have TPKS activity. The selection of cells or cell lines for use in preparing a cDNA library to isolate TPKS cDNA may be done by first measuring cell associated TPKS activity using incorporation of radiolabelled acetate and separation of products by high performance liquid chromatography (HPLC).

Preparation of cDNA libraries can be performed by standard techniques well known in the art. Well-known cDNA library construction techniques can be found for example, in Maniatis, T., Fritsch, E. F., Sambrook, J., *Molecular Cloning: A Laboratory Manual* (Cold Spring Harbor Laboratory, Cold Spring Harbor, N.Y., 1982).

It is also readily apparent to those skilled in the art that DNA encoding TPKS may also be isolated from a suitable genomic DNA library. Construction of genomic DNA libraries can be performed by standard techniques well-known in the art. Well-known genomic DNA library construction techniques can be found in Maniatis et al., (supra).

In order to clone the TPKS gene, knowledge of the amino acid sequence of TPKS may be necessary. To accomplish this, TPKS protein may be purified and partial amino acid sequence determined by conventional methods. Determination of the complete amino acid sequence is not necessary. Once suitable amino acid sequences have been identified, the DNA sequences capable of encoding them are synthesized.

Because the genetic code is degenerate, more than one codon may be used to encode a particular amino acid, and therefore, the amino acid sequence can be encoded by any of a set of similar DNA oligonucleotides. Only one member of the set will be identical to the TPKS sequence but will be capable of hybridizing to TPKS DNA even in the presence of DNA oligonucleotides with mismatches. The mismatched DNA oligonucleotides may still hybridize to the TPKS DNA to permit identification and isolation of TPKS encoding DNA.

It is readily apparent to those skilled in the art that DNA encoding TPKS from a particular organism may be used to isolate and purify homologues of TPKS from other organisms. To accomplish this, the first TPKS DNA may be mixed with a sample containing DNA encoding homologues of TPKS under appropriate hybridization conditions. The hybridized DNA complex may be isolated and the DNA encoding the homologous DNA may be purified therefrom.

cDNA clones encoding TPKS may be isolated in a two-stage approach employing polymerase chain reaction (PCR) based technology and cDNA library screening.

Amino acid sequence information may be obtained by automated amino acid sequencing using Edman chemistry of both the intact protein and the peptide fragments generated by specific proteolytic cleavage. Following incubation for the prescribed periods, digestion is terminated and resulting peptide fragments are fractionated and detected.

TPKS in substantially pure form derived from natural sources according to the purification processes described herein, is found to be encoded by a single mRNA.

The cloned TPKS cDNA obtained through the methods described above may be expressed by cloning it into an expression vector containing a suitable promoter and other appropriate transcription regulatory elements, and transferred into prokaryotic or eukaryotic host cells to produce recombinant TPKS. Techniques for such manipulations are well-known in the art.

In order to simplify the following Examples and the Detailed Description, certain terms will be defined.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells and animal cells. Expression vectors include, but are not limited to, cloning vectors, modified cloning vectors, specifically designed plasmids or viruses. Specifically designed vectors allow the shuttling of DNA between hosts, such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters.

An expression vector is a replicable DNA construct in which a DNA sequence encoding a TPKS is operably linked to suitable control sequences capable of effecting the expression TPKS in a suitable host. Control sequences include a transcriptional promoter, an optional operator sequence to control transcription and sequences which control the termination of transcription and translation.

Certain vectors, such as amplification vectors, do not need expression control domains but rather need the ability to replicate in a host, usually conferred by an origin of replication, and a selection gene to facilitate recognition of transformants.

A promoter is defined as a DNA sequence that directs RNA polymerase to bind to DNA and initiate RNA synthesis. A strong promoter is one which causes mRNAs to be initiated at high frequency.

DNA encoding TPKS may also be cloned into an expression vector for expression in a host cell. Host cells may be prokaryotic or eukaryotic, including but not limited to bacteria, yeast, mammalian and insect cells and cell lines.

The expression vector may be introduced into host cells via any one of a number of techniques including but not limited to transformation, transfection, protoplast fusion, and electroporation. The expression vector-containing cells are clonally propagated and individually analyzed to determine whether they contain the TPKS gene or produce TPKS protein. Identification of TPKS expressing host cell clones may be done by several means, including but not limited to immunological reactivity with anti-TPKS antibodies, and the presence of host cell-associated TPKS activity.

Expression of TPKS DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with micro-injection into frog oocytes being preferred.

PCR is the polymerase chain reaction, which is a technique for copying the complementary strands of a target DNA molecule simultaneously for a series of cycles until the desired amount is obtained.

Plasmids are generally designated by a low case p preceded or followed by capital letters and/or numbers. The starting plasmids used in this invention are commercially available, are publicly available on an unrestricted basis, or can be constructed from such available plasmids by conventional procedures. In addition other equivalent plasmids or constructs will be readily apparent to one skilled in the art.

Transformed host cells are cells which have been transformed or transfected with TPKS vectors constructed using recombinant DNA techniques. Expressed TPKS may be deposited in the cell membrane of the host cell or may be intracellular or may be secreted.

It is also well known, that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is also well known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate. Alteration of the amino acid sequence may lead to altered properties that in turn result in the production of modified structures; for example, the elimination of one of the reductase activities may result in the biosynthesis of a less-reduced compound.

The full-length TPKS-encoding DNA in plasmid pLOA was designated pTPKS100. A sample of pTPKS-100 in E. coli strain JM109, was deposited under the terms of the Budapest Treaty, on Sep. 15, 1993 in the permanent culture collection of the American Type Culture Collection, at 12301 Parklawn Drive, Rockville, Md., 20852, and has been assigned the Accession number ATCC 69416.

The following examples illustrate the present invention without, however, limiting the same thereto.

EXAMPLE 1

Culture Conditions

Three strains of Aspergillus terreus were used. The two lovastatin-producing strains included A. terreus ATCC 20542. A lovastatin nonproducing strain was also used. A lovastatin-nonproducing strain or a lovastatin-overproducing strain of A. terreus may be derived from lovastatin-producing strains of A. terreus that are publicly available; an example of a publicly-available strain is A. terreus MF4833, which is deposited with the American Type Culture Collection under Accession No. 20542. One skilled in the art would appreciate that a variety of techniques such as mutagenesis techniques, including but not limited to ultraviolet irradiation, treatment with ethylmethanesulfonate (EMS), exposure to nitrous acid, nitrosoguanidine and psoralen-crosslinking, could be used to generate a strain that does not produce or which overproduces lovastatin. The extent of the mutagenesis may be determined in a variety of ways including auxotrophy, i.e., the requirement of the mutated strain for a specific growth substance beyond the minimum required for normal metabolism and reproduction of the parent strain as well as measurement of production of lovastatin by individual cultures. An alternative monitoring system involves the use of an intercalating dye such as acriflavine, which prevents any growth of the parent (lovastatin-producing) strain when plated at 10,000 spores per plate but, following mutagenesis, allows growth of about 3–5 colonies per plate. Alternatively, the extent of mutagenesis may be monitored by visual observation of colonies having morphologies or colors that differ from the unmutagenized parent strain. Mutant strains are reisolated and pooled and subjected to further mutagenesis so that, by repetition of these procedures, mutated strains of A. terreus that do not produce or which overproduce lovastatin may be obtained.

Monascus ruber ATCC 20657 and Penicillium citrinum ATCC 20606 were used in hybridization studies.

The strains were maintained on YME+TE medium. The recipe for YME+TE medium is as follows:

0.4% Yeast Extract (w/v);

1.0% Malt Extract (w/v);

0.4% Glucose (w/v);

0.5% Trace Element (TE; v/v); and 2.0% agar (w/v) in 1 liter of water, pH 7.2.

The recipe for Trace Elements (TE) is as follows:

0.1% $FeSO_4$-$7H_2O$ (w/v);

0.1% $MnSO_4$-$H_2O$ (w/v);

0.0025% $CuCl_2$.$2H_2O$ (w/v);

0.0132% $CaCl_2$.$2H_2O$ (w/v);

0.0056% $H_3BO_3$ (w/v);

0.0019% $(NH_4)_6Mo_7O_{24}$.$4H_2O$ (w/v); and 0.02% $ZnSO_4$.$7H_2O$ (w/v) in 1 liter of water.

EXAMPLE 2

Fermentation Conditions

For the generation of spore stocks, single colonies were generated by growing on YME+TE plates for 8 days at 28° C. and 65% relative humidity. Single colonies were removed, and streaked on YME+TE slants. The slants were incubated for 8 days at 28° C. in 65% humidity. Spores were harvested by addition of 2 ml of Spore Suspension Solution (SSS). SSS contains 10% Glycerol (v/v) and 5% Lactose (w/v) in water. Spores were scraped into the SSS with a sterile inoculation loop and counted. The suspension was stored at −20° C.

A two-stage fermentation from spore suspensions was used for the production of lovastatin. A seed culture was started by inoculating $1 \times 10^8$ spores into 2 ml/15 ml culture tube of HLC medium.

The recipe for HLC medium is as follows:

1.5% $KH2PO_4$ (w/v);

2.0% Cerelose (w/v);

0.1% Ardamine pH (Champlain Industries) (w/v);

1.5% Pharmamedia (Traders Protein) (w/v);

0.2% Lactic acid (v/v); and 0.4% ammonium citrate (w/v) in 1 liter of water.

The pH of HLC medium was adjusted to pH 7.2 before sterilization.

Cultures were shaken at a 30 degree angle at 28° C. for approximately 28 hours on a rotary shaker with a 70 mm diameter amplitude at 220 rpm. Two ml of seed culture was used to inoculate 25 ml of GP-9 medium in a 250 ml flask.

The recipe for GP-9 medium is as follows:

0.9% Ammonium Citrate (w/v);

0.12% Ardamine pH (w/v);

1.2% Cerelose (w/v);

4.0% Pharmamedia (w/v);

24.5% Lactose (w/v); and 0.2% P 2000 (v/v) in water at pH 7.2.

Incubation was continued as described for seed cultures without the 30 degree angle. Lovastatin production was monitored after 12 days of fermentation.

A one stage fermentation of *A. terreus* cultures in CM media was used to generate vegetative mycelia for transformations or DNA preparations. Fermentations were started by inoculating $1\times10^8$ conidiospores into 50 ml of CM medium in a 250 ml flask and incubated as described.

The recipe for Complete Medium (CM) is as follows:

50 ml of Clutterbuck's salts;

2.0 ml Vogel's Trace elements;

0.5% Tryptone (w/v);

0.5% Yeast extract (w/v); and 1.0% Glucose (w/v) in one liter of water.

The recipe for Clutterbuck's salts is as follows:

12.0% $Na_2NO_3$ (w/v);

1.02% KCl (w/v);

1.04% $MgSO_4 \cdot 7H_2O$ (w/v); and 3.04% $KH_2PO_4$ (w/v).

The recipe for Vogel's trace elements is as follows:

0.004% $ZnCl_2$ (w/v);

0.02% $FeCl_3$ (w/v);

0.001% $CuCl_2$ (w/v);

0.001% $MnCl_2 \cdot 4H_2O$;

0.001% $NaB_4O_7 \cdot 10H_2O$ (w/v); and 0.001% $(NH_4)_6MO_7O_{24} \cdot 7H_2O$ (w/v).

EXAMPLE 3

Construction of Vector, pLO9 pLO9 is a 5.6 kb vector constructed with features useful for both cosmid library construction and fungal transformations. For dominant selection in *Aspergillus terreus*, pLO9 contains a *Streptoalloteichus hindustanus* phleomycin resistance gene driven by an *A. niger* β-tubulin promoter and terminated by a *Saccharomyces cerevisiae* terminator sequence. For selection in *Escherichia coli*, the vector contains the ampicillin resistance gene and for lambda packaging, the vector contains a lambda cos site. The construction of pLO9 is described below.

The phleomycin resistance marker originated from *S. hindustanus* and the termination sequence is from the CYC1 gene in *S. cerevisiae*. Both sequences were isolated on one DNA fragment from pUT713 (CAYLA, Toulouse Cedex, France) by digesting pUT713 with the restriction enzymes BamH1 and BglII. The isolated fragment was cloned into BamH1-digested pUC18 to produce vector pLO1. The genomic copy of the β-tubulin gene from *A. niger* ATCC 1015, was cloned as a 4.3 kb EcoR1 fragment in pUC8 to create p35-C-14. Several modifications were made to the genomic sequence. An EcoRI site was introduced at the initiator ATG by in vitro mutagenesis. The HindIII site in the promoter was removed by digestion with exonuclease, filling in with Klenow, and religation. Finally, an upstream EcoRI site was changed to a PstI site by digestion with EcoRI, filling in with Klenow and addition of a PstI linker by religation with ligase. The β-tubulin promoter was then subcloned as a PstI to EcoRI fragment in pUC8 to create pC15-1. An XbaI site was introduced at the initiator ATG by digestion with EcoRI, filling in with Klenow, addition of a XbaI linker and religation. The resulting vector was named pTL-113.

The β-tubulin promoter was cloned upstream of the phleomycin gene by cutting pTL113 with PstI and XbaI and cloning the isolated promoter fragment into the PstI and XbaI sites of pLO1 to produce pLO3. The BglII site was removed with a fill in reaction followed by blunt-end ligation to produce vector pCS12. The PstI to HindIII fragment containing the beta tubulin promoter, phleomycin resistance gene, and the terminator sequence were cloned into a pUC8 vector to generate pLO6. The XbaI site at the ATG was removed by a fill-in reaction and ligation to give pLO7. The PstI to HindIII was moved as a fragment into a pUC18 backbone in which the XmaI site had been filled and replaced with a BglII linker. The resulting vector was named pLO8. A PstI fragment containing the lambda cos site from pJL21 was inserted into the vector to generate pLO9.

EXAMPLE 4

Isolation of Genomic DNA

Vegetative mycelia were generated in CM media for 48 hr at 220 rpm at 28° C. Mycelia were collected by filtration through cheesecloth and frozen in liquid nitrogen for lyophilization overnight. Lyophilized mycelia were ground with sand using a mortar and pestle and suspended in 5 ml of Breaking Buffer (100 mM NaCl; 50 mM EDTA; 10 mM Tris, pH 8.0; 1% SDS; 50 ug/ml pancreatic RNase; 50 ug/ml Proteinase K). The mix was transferred to a 125 ml flask and an equal volume of Tris-saturated phenol/chloroform (50:50) was added. The flask was shaken for 1 hour at 37° C. and 200 rpm. The aqueous layer was removed after centrifugation at 10,000 rpm for 10 minutes. The aqueous layer was extracted twice more with phenol/chloroform and was then extracted once with chloroform. DNA was precipitated from the aqueous layer by addition of 0.1 volume 3M NaCl and 2.5 volumes of ethanol and then freezing at −70° C. for 10 minutes. The precipitated DNA was collected by centrifugation at 10,000 rpm for 15 minutes. The pelleted DNA was dried and resuspended in a solution of 10 mM Tris-HCl, 1 mM EDTA, pH 7.5. DNA concentrations were determined by measuring absorbance at wavelength 260 nM.

EXAMPLE 5

Construction of *A. terreus* Libraries

A. Preparation of Genomic Fragments

*A. terreus* genomic DNA was isolated as described. Large random DNA fragments for insertion into the vectors were isolated by partially digesting 10 μg of DNA with the restriction enzyme Sau3A. The digested DNA was electrophoresed on a 1.0% Agarose gel. For the genomic library, an area containing 9–23 kb sized fragments was cut from the gel. For the cosmid library, another segment of the gel containing 30–60 kb sized fragments was excised. The large chromosomal DNA fragments contained in the gel slices were isolated by electroelution. The DNA was concentrated by addition of 0.1 volumes of 3M sodium acetate and 2.5 volumes of ethanol, freezing at −70° C. for 15 minutes, and centrifugation at 10,000 rpm for 10 minutes to precipitate the DNA.

B. Construction of the *A. terreus* Cosmid Library

The pLO9 cosmid DNA was used to supply the two arms and cos sites required for lambda packaging. Two fragments were isolated from pLO9 for the packaging reaction.

Fragment one was isolated by digesting pLO9 with Xba1, phosphatasing with HK phosphatase (Epicenter Technologies), digesting with BglII, electroeluting on a 1% Agarose gel, concentrating by the addition of 0.1 volumes of 3M sodium acetate and 2.5 volumes of ethanol, freezing at −70° C. for 15 minutes and centrifuging at 10,000 rpm for 10 minutes to precipitate the DNA.

Fragment two was isolated by digesting pLO9 with SmaI, phosphatasing with HK phosphatase and then digesting with BgIII. Fragment two was isolated with the procedure described for fragment one. Fragment one, fragment two and isolated *A. terreus* insert DNA were ligated in a 1:1:2 ratio at a concentration of 0.5 µg of each DNA.

C. Packaging into Lambda Phage and Plating

Packaging into lambda phage was accomplished by mixing the ligation mixture with 10 µl of extract A from *E. coli* strain BHB2688 (Amersham) and 15 µl of extract B from *E. coli* strain BHB2690 (Amersham). The packaging mix was incubated at 22° C. for 120 minutes. A volume of 500 µl of SM (0.58% NaCl(w/v); 0.20% $MgSO_4$(w/v); 0.05M Tris pH 7.5; 0.01% Gelatin(w/v)) and 10 µl of chloroform was then added to the packaging mix.

*E. coli* strain DH5 was prepared for transfection by growing cells to an optical density of 1.0 at wavelength 600 nm in LB+maltose medium. LB+maltose medium consists of 1.0% Bacto-tryptone (w/v); 0.5% Bacto-yeast extract (w/v); 1.0% NaCl (w/v); pH 7.5; 0.2% Maltose (v/v) is added after autoclaving.

The cells were centrifuged at 4,000 rpm for 10 minutes and resuspended in 10 mM $MgSO_4$. Fifty microliters of the packaging mix was added to 200 µl of the resuspended DH5 cells and incubated for 30 minutes at 37° C. A 500 µl of aliquot of LB medium was added and the mix was incubated for 30 minutes at 37° C. The cell mix was spread on LB agar plates containing 100 µg/ml ampicillin (Sigma) and incubated at 37° C. A total of 10,000 colonies were generated with this library.

D. Construction of the *A. terreus* Genomic Library

The lambda replacement vector, EMBL3 (Promega), was used for the construction of the genomic library. The vector was purchased as predigested arms ready for ligation with the genomic inserts. The two arms were ligated to the 9–23 kb genomic inserts at a ratio of 1:1:2, packaged into lambda phage, and plated for hybridization with selected probes as described above.

EXAMPLE 6

A. Isolation of Cosmid DNA from *E. coli*

The *A. terreus* cosmid library in *E. coli* was grown on 25 cm×25 cm plates containing 200 ml LB agar supplemented with 100 µg/ml ampicillin added. Nearly confluent colonies were scraped from plates in 10 ml of cold TS solution (50 mM Tris, pH 8.0 and 10% Sucrose(w/v)). A 2.0 ml aliquot of 10 mg/ml lysozyme made in 0.25M Tris, pH 8.0 was added; then 8 ml of 0.25M ethylenediamine tetraacetic acid (EDTA) was added. The mix was inverted several times and incubated on ice for 10 minutes. A 4 ml aliquot of a 10% SDS solution was added slowly while mixing gently with a glass rod. Next, 6.0 ml of 5M NaCl was added slowly while mixing with a glass rod. The cell lysate was incubated on ice for 1 hour and then centrifuged. The supernatant was saved and then extracted twice with an equal volume of Tris-saturated Phenol/Chloroform (50:50). DNA was precipitated by adding 2 volumes of ethanol, freezing at −70° C. for 15 minutes and then centrifuging at 3,000 rpm for 15 minutes. The precipitated cosmid DNA was dried and resuspended in 9 ml of Tris-EDTA.

Cosmid DNA was prepared for cesium chloride density gradient purification by dissolving 10 gm of CsCl2 in the DNA suspension and then adding 250 µl of 10 mg/ml ethidium bromide. Cosmid DNA was banded with a 20 hour centrifugation in a Ti865.1 Sorvall rotor at 55,000 rpm. The DNA bands representing cosmid DNA were recovered from the gradient, and ethidium bromide was removed by extraction with water-saturated butanol. Cosmid DNA was precipitated by adding 3 volumes of water and 10 volumes of ethanol, incubating on ice for 30 minutes and then centrifuging. The DNA was resuspended in Tris-EDTA and reprecipitated by the addition of 0.1 volume of 3M sodium acetate and 2.5 volumes of ethanol. DNA was frozen at −70° C. for 10 minutes, centrifuged, and resuspended in Tris-EDTA.

The DNA preparation was electrophoresed through a 0.5% Low Melting Temperature Agarose (BioRad) gel to eliminate contamination by pLO9 DNA. The band containing cosmid DNA with inserts was cut from the gel and heated to 65° C. with 2 volumes of Tris-EDTA. The melted agarose was extracted 3 times with Tris-saturated phenol and then once with chloroform. Cosmid library DNA was precipitated by addition of 0.1 volumes of 3M sodium acetate and 2.5 volumes of ethanol, freezing at −70° C. for 15 minutes, and centrifuging at 10,000 rpm for 15 minutes. The DNA was dried and resuspended in Tris-EDTA. The concentration of DNA was determined by measuring the optical density at 260 nm.

EXAMPLE 7

Transformation of *A. terreus*

Cultures were grown by inoculating $1 \times 10^8$ conidiospores into 50 ml of CM media in a 250 ml Erlenmeyer flask. Cultures were grown for between 24 and 30 hr at 200 rpm and 28° C. Mycelia were harvested by gravity filtration through Miracloth. Mycelia (4 g) were transferred to a 500 ml Erlenmeyer flask containing 100 ml KMP. KMP consists of 700 mM KCl, 800 mM Mannitol, and 20 mM $KH_2PO_4$ pH 6.3. Lysing Enzymes from *Trichoderma harzianum* (100 mg; Sigma) was added. Flasks were shaken at 100 rpm for 18 hours at 28° C.

Spheroplasts were harvested by gravity filtration through Miracloth. The filtrate was collected in 50 ml conical centrifuge tubes, concentrated by centrifugation and washed by resuspending the spheroplasted cells in 15 ml of KCM solution. KCM consists of 700 mM KCl; 10 mM MOPS adjusted to pH 5.8. The washing was repeated twice. Washed spheroplasts were resuspended at a concentration of $5 \times 10^7$/ml in KCMC. KCMC consists of 5% 1M $CaCl_2$ and 95% KCM.

For each transformation, a sample of 5 µg of DNA was brought to a volume of 20 µl in Tris-EDTA; then 5 units of heparin in 6.5 µl of KCMC was added. Next, 200 µl aliquot of the spheroplast suspension was added to the DNA-containing solution. Finally, 50 µl of aliquot of a solution containing 5% 1M $CaCl_2$ and 95% PCMC (40% PEG 8,000; 10 mM MOPS, pH 5.8; 0.05M $CaCl_2$) was added. The mixture was incubated on ice for 30 minutes.

An aliquot (600 µl) of the KCMC solution was added to a 45° C. equilibrated solution of MA. MA consists of 5% Clutterbuck's salts(v/v); 0.5% Tryptone (w/v); 0.5% Yeast Extract (w/v); 1.0% Glucose(w/v); 23.4% Mannitol(w/v) and 3% Agar. This suspension was divided among 5 pre-weighed petri dishes and incubated at 28° C. for 4 hours. The weight of agar in each plate was determined by a second weight and an equal amount of Overlay (OL) consisting of: 1% Peptone (w/v); 1% Agar (w/v); with between 100 µg/ml and 150 µg/ml (strain ATCC 20542) of phleomycin was added to each petri dish. Petri dishes were incubated at 28° C. and 65% humidity for 7–10 days before transformed colonies were picked.

EXAMPLE 8

Rescue of Cosmid DNA from *A. terreus*

The transforming cosmid DNA was rescued from an *A. terreus* transformants by isolating chromosomal DNA and packaging into lambda phage particles. Isolation of genomic DNA and packaging into lambda phage were performed as described above.

EXAMPLE 9
Detection of Lovastatin

Fermentation extracts were prepared by adding two volumes of reagent alcohol to the fermentation flasks and shaking the flasks were shaken for 15 minutes at 220 rpm and 28° C. The contents were allowed to settle for 15 minutes and 1 ml of the liquid was removed. The sample was diluted 1/20 in methanol, filtered and then analyzed by HPLC. Lovastatin was detected by a Waters HPLC using a 8 mm×10 cm C18 4 um Waters Novapak column. Mobile phases were A: Acetonitrile with 0.02% Trifluoroacetic acid and B: Distilled water with 0.02% Trifluoroacetic acid. Gradients were run at a flow rate of 1.5 ml/min. Initial conditions were 35% A and 65% B and were held for 1 minute after sample injection. A gradient was formed to 65% A and 35% B over 3 minutes and held for 3.6 minutes. Lovastatin ammonium salt was detected at 239 nm.

EXAMPLE 10
Southern Analysis of DNA

Southern analysis was performed by electrophoresing 5 μg of digested DNA on a 1.0% agarose gel in TAE buffer (0.04M Tris and 0.002M EDTA). DNA in the gel was denatured by soaking the gel in Solution A (1.5M NaCl and 0.5M NaOH) for 30 minutes. The gel was then neutralized in Solution B (1.0M Tris and 1.5M NaCl) for 30 minutes. DNA was transferred to nitrocellulose or nylon membranes by blotting overnight with a 10×SCC solution. SSC consists of 8.75% NaCl (w/v) and 4.4% sodium citrate (w/v), pH 7.0. DNA was baked onto the nitrocellulose at 80° C. under vacuum for 30 minutes.

Standard hybridization conditions were as described in Sambrook, J. et al., (*Molecular Cloning,* 1989 (ed. Chris Nolan) Cold Spring Harbor Press). Membranes were prepared for hybridization by incubating at 42° C. in hybridization buffer consisting of: 6×SSC, 5×Denhardt's reagent, 0.5% SDS, 100 μg/ml denatured and fragmented salmon sperm DNA, and 40% formamide. After incubating for two hours, the denatured labeled probe was added and further incubated overnight at 42° C. Unless otherwise stated, the filters were washed twice in 6×SSC and 0.1% SDS at room temperature for 15 minutes followed by two 30 minute washes at 42° C. in 0.1×SSC and 0.5% SDS. Filters were exposed to X-ray film for visualization of the signal.

EXAMPLE 11
A. Isolation of Triol Polyketide Synthase from *A. terreus*

Mycelia of *A. terreus* were grown in GP-9 medium. After 48 hours the mycelia were collected by vacuum filtration, washed with cold water, frozen in liquid nitrogen and lyophilized. All subsequent steps of the purification were performed on ice or at 3° C. unless otherwise noted.

Lyophilized mycelia (6 g) were homogenized by grinding with 20 gm glass beads (0.2 mm) in a mortar with pestle in 135 ml homogenization buffer consisting of: 20 mM Tris, pH 8; 10% glycerol; 5 mM EDTA; 50 mM NaCl; 5 mM ascorbic acid; 3.8 μg/ml leupeptin; 17.7 μg/ml chymostatin; 2.0 μg/ml pepstatin, 42 μg/ml turkey trypsin inhibitor, 0.2 mM PMSF; and 2.2% (dry wt/v) hydrated polyvinyl polypyrrolidone. The homogenate was centrifuged at 7,650×g for 10 minutes; and the supernatant applied to an SH-affinity column (Affi-gel 501 organomercurial agarose; Bio-Rad; 1.5×8.0 cm) equilibrated in Buffer A. Buffer A consists of 20 mM Tris, pH 8; 50 mM NaCl; 5 mM EDTA; 5 mM ascorbic acid; at 30 ml/hr. The column was washed with 25 ml Buffer A followed by 75 ml Buffer A containing 0.5M NaCl. After reequilibrating the column with 50 ml Buffer A, bound proteins were eluted with 40 ml Buffer A supplemented with 100 mM dithiothreotol (DTT). The eluted protein fraction was made 4.2 μg/ml leupeptin; 2 μg/ml pepstatin; 18 μg/ml chymostatin; 0.2 mM PMSF and then was pelleted by ultracentrifugation at 180,000×g for 16 hr. The supernatant was discarded, and the pellet was rinsed with a buffer consisting of 20 mM Tris, pH 8; 5 mM ascorbic acid; 1 mM DTT; 1 mM EDTA. The washed pellet was resuspended in 2 ml of buffer consisting of 40 mM Tris, pH 6.8; 20 mM DTT; 2% SDS, then heated to 90° C. for 10 minutes and put on ice.

A 250 μl aliquot of the resuspended pellet was combined with an equal volume of sample buffer (125 mM Tris, pH 6.8; 20% glycerol; 0.005%(w/v) bromphenol blue; 4%(w/v) SDS; 1.5M beta mercaptoethanol) and heated to 95° C. for 10 minutes. The sample was electrophoresed on a preparative 1.5 mm, 4% acrylamide SDS precast gel (Novex) at 145V for 2 hr using Laemmeli electrode buffer system (25 mM Tris; 192 mM glycine; 0.1% SDS). When a prestained 200 kD reference standard was 1.4 cm from the bottom of the gel, the electrophoresis was terminated.

Proteins were visualized as follow. The gel was rinsed for 5 seconds in distilled $H_2O$, then rinsed for 10 minutes in 0.2M imidazole with shaking and was then transferred to a solution of 0.3M zinc acetate for 5 minutes with shaking. The gel was then rinsed in water. The TPKS, which ran with an apparent molecular weight of 235 kD, was localized to a relative mobility position of 0.53 (relative to the bottom of the gel). The TPKS protein was the protein of greatest abundance on the gel; no significant protein banding was seen with lower $R_f$. The apparent 235 kD protein band was excised from the gel and was then destained in 0.25M Tris and 0.25M EDTA pH 9.5 for approximately 5 minutes.

The destained gel slice was crushed between two glass plates and placed in a 50 ml tube containing 5 ml of 20 mM Tris, 5 mM EDTA, 0.1% SDS, pH 8.0. The tube was shaken on a rotary shaker for 48 hours at 37° C. Gel fragments were removed by centrifugation, and the supernatant containing the eluted protein was concentrated to 100 μl with a Centricon 30 microconcentrator (Amicon).

B. Molecular Weight Determination

The gel-purified protein was resuspended in Laemmli load buffer, heated to 95° C. for 5 min. and then electrophoresed on a 4–15% gradient SDS polyacrylamide gel (BioRad Ready-Gel) in Laemmli electrode buffer. After staining, the molecular weight of the protein was determined by comparison to molecular weight standard proteins.

C. Antibody Production

The TPKS protein was prepared via preparative SDS-PAGE as described, except the protein was not electroeluted from the acrylamide gel matrix. Following destaining, the gel slice was crushed between two glass plates, and first forced through a 18 gauge syringe needle and then through a 25 gauge syringe needle. A 0.5 ml aliquot of the 25 gauge needle eluate was mixed with an equal volume of Freund's complete adjuvant and injected intradermally at five sites of a New Zealand white male rabbit. Boosts were done at 21 and 42 days using protein prepared as described, but mixed with 0.5 ml of Freund's incomplete adjuvant. Ten days after the final boost the rabbit was exsanguinated and the antiserum collected.

D. Affinity Purification of Antibody

Affinity purified antibody was prepared by immobilizing the TPKS protein to PVDF membrane by transfer from a preparative SDS polyacrylamide gel. The TPKS was visualized and that area of the membrane cut out. After blocking in 5%(w/v) non-fat dry milk in TTBS for 1 hour, the membrane was washed 3×5 minutes in TTBS. A 2 ml aliquot of antisera was diluted 1:1 with TTBS supplemented with 1% (w/v) non-fat dry milk and incubated with the immobilized antigen for 5 hours. The membrane was then washed 4× (10 minutes per wash) with TTBS, and the bound antibody was eluted with 2 ml of 0.1M glycine, pH 2.8. The eluted antibody was neutralized with 50 µl of 1.0M Tris, pH 9.5 and concentrated twenty-fold.

E. Western Blot Analysis

Purified TPKS protein and partially purified protein preparations of organomercurial eluates were resolved by 4% acrylamide SDS-PAGE (NOVEX, precast 1.0 mm thick gels) and then transferred to nitrocellulose in Towbin transfer buffer (25 mM Tris; 192 mM glycine, pH 8.3; 20% methanol; 0.05% SDS) at 240 mA for 2 hr. All subsequent steps were done at room temperature with shaking.

The nitrocellulose blot was rinsed for 1 minute in TBS (50 mM Tris, pH 7.5; 0.5M NaCl) and then blocked for 2 hours in TBS supplemented with 0.05% Tween 20 (TTBS) and 5% (w/v) non-fat dry milk. The blot was incubated with the primary antibody (a 1:1000 dilution of rabbit antisera in TTBS containing 1% (w/v) non-fat dry milk) for 16 hr. The blot was washed in TTBS 3 times for 5 min. The blot was incubated with the second antibody (goat anti-rabbit alkaline phosphatase conjugate diluted 1:1000) for 2 hr in TTBS supplemented 1% (w/v) non-fat dry milk. After washing 4 times (10 minutes per wash) in TTBS, color development was achieved with 5-bromo-4-chloro-3-indolyl phosphate (115 µg/ml) and nitroblue tetrazolium (330 µg/ml) in 66 mM Tris, pH 9.5; 0.1M NaCl; 5 mM $MgCl_2$.

EXAMPLE 12

Isolation of Aspergillus RNA

A. Isolation of Total RNA

*A. terreus* was grown for 48 hours in 25 ml of GP-9 fermentation medium at 28° C. and 220 rpm on a rotary shaker. Mycelia were collected by vacuum filtration through Miracloth and cheesecloth and washed with approximately 100 ml distilled water. The mycelia were scraped from the filter into a plastic beaker and frozen with liquid nitrogen. Frozen mycelia were stored at −80° C. until needed.

Frozen mycelia were weighed and placed in a mortar chilled with liquid nitrogen. Approximately 2 g of 0.2 mm glass beads were added, and the mix was ground to a fine powder with a pestle. Liquid nitrogen was added as needed to keep the mycelia frozen at all times. Ground mycelia were added to a flask containing approximately 2.5 ml/g Breaking Buffer (50 mM Tris pH 7.4; 150 mM NaCl; 5 mM EDTA; 5% SDS(w/v)) and an equal volume of Tris-saturated phenol:chloroform:isoamyl alcohol (50:50:1), and vanadyl ribonucleoside complex (BRL) to a final concentration of approximately 2 mM. The mixture incubated on a rotary shaker at 37° C. for 20 minutes and was then centrifuged at 12000×g for 10 min at 4° C. The aqueous layer was removed and extracted with an equal volume of Tris-saturated phenol:chloroform:isoamyl alcohol (50:50:1). Second and third extractions were done with 1M Tris-saturated phenol:chloroform (50:50) and chloroform, respectively. The final aqueous layer was mixed with an equal volume of 6M LiCl and left at −20° C. for at least 4 hours. The precipitate was pelleted at 12,000×g for 20 minutes at 4° C. and resuspended in 0.6 ml water treated with 0.1% diethyl pyrocarbonate (DEPC). The total RNA was reprecipitated with 0.1 volume of sodium acetate and 2.5 volumes ethanol. The final pellet was dissolved in 0.3 ml water treated with 0.1% DEPC.

B. Isolation of Polyadenylated RNA

Polyadenylated RNA was isolated by heating approximately 500 µg of total RNA in 0.2 to 1.0 ml water to 65° C. for 5 minutes, cooling on ice, and adding 10× sample buffer consisting of: 10 mM Tris pH 7.5; 1 mM EDTA; 5M NaCl in 0.1% DEPC-treated water to a final concentration of 1×. The treated sample was applied to a column of oligod(T) cellulose prepared according to the manufacturer's instructions (Poly(A)Quik™ mRNA purification kit—Stratagene). The column was washed twice with High Salt Buffer (10 mM Tris pH 7.5; 1 mM EDTA; 0.5M NaCl) and three times with Low Salt Buffer (10 mM Tris pH 7.5; 1 mM EDTA and 0.1M NaCl). PolyA mRNA was then eluted from the column with four 200 µl aliquots of Elution Buffer (10 mM Tris pH 7.5 and 1 mM EDTA) which had been heated to 65° C. RNA concentration was determined spectrophotometrically using absorbance at 260 nm.

EXAMPLE 13

Construction of Lambda gt-11 cDNA Library

A cDNA library was constructed using 4 to 5 µg of polyadenylated RNA that had been purified twice over an oligo(dT) column. The reagents for construction of cDNA, addition of adapters and ligation of lambda gt-11 arms except [$^{32}$P]dCTP were provided in the Superscript™ Choice System (BRL) and were used according to the manufacturer's instructions.

First strand synthesis was primed using either 0.05 µg random hexamers plus 0.5 µg oligo(dT)12–18 or 1 µg oligo(dT)12–18 alone. The reaction was carried out in a final volume of 20 µl (final composition: 50 mM Tris, pH 8.3; 75 mM KCl; 3 mM $MgCl_2$; 10 mM DTT; 500 uM each dATP, dCTP, dGTP, dTTP; primers; mRNA; 10 µCi [$^{32}$P]dCTP; 200 U Superscript™ reverse transcriptase/µg mRNA). The reaction mixture was incubated for 1 hr at 37° C. and then placed on ice.

Second strand synthesis was carried out in a final volume of 150 µl using 18 µl of the first strand reaction. The final composition of the reaction was: 25 mM Tris pH 7.5; .100 mM KCl; 5 mM $MgCl_2$; 10 mM $(NH_4)_2SO_4$; 0.15 mM B-NAD+; 250 µM each dATP, dCTP, dGTP, dTTP; 1.2 mM DTT; 65 U/ml DNA Ligase; 250 U/ml DNA polymerase I; and 13 U/ml RNase H. This reaction mixture was incubated at 16° C. for 2 hr; then 10 U of T4 DNA polymerase was added, and the incubation was continued at 16° C. for an additional 5 minutes. The reaction was put on ice and stopped by adding 10 µl of 0.5M EDTA. The mix was extracted with 150 µl of Tris-saturated phenol:chloroform:isoamyl alcohol (25:24:1). The aqueous layer was removed, and cDNA was precipitated with 0.5 volume 7.5M ammonium acetate and 3.5 volumes ethanol. The cDNA pellet was washed with 70% ethanol. EcoRI (Not1) adapters were ligated to the cDNA in a reaction mix comprised of 66 mM Tris, pH 7.6; 10 mM $MgCl_2$; 1 mM ATP; 14 mM DTT; 200 µg/ml EcoRI (Not1) adapters; 100 U/ml T4 DNA ligase. The reaction mixture was incubated for 16 hours at 16° C., then heated to 70° C. and placed on ice. The adapted cDNA was phosphorylated by adding 30 U of T4 polynucleotide kinase to the reaction mix and incubating for 30 minutes at 37° C. The kinase was inactivated by heating to 70° C. for 10 minutes. The completed reaction was diluted with 97 µl of TEN buffer (10 mM Tris, pH 7.5; 0.1 mM EDTA; 25 mM NaCl) and placed over a Sephacryl® DNA sizing column prepared according to the manufacturer's directions (BRL). The DNA was eluted with TEN buffer and fractions were collected. Cerenkov counts were obtained for each fraction and the amount of cDNA/fraction was calculated. The column fractions were pooled in order of elution until 50 ng cDNA was collected. The pool was then precipitated with 5

μl yeast tRNA, 0.5 volumes 7.5M ammonium acetate and 2 volumes ethanol (−20° C.). The resultant pellet was washed with 70% ethanol, dried and ligated to lambda gt-11 arms. The final composition of the ligation reaction was 50 mM Tris pH 7.6; 10 mM MgCl$_2$; 1 mM ATP; 5% PEG 8000(w/v); 1 mM DTT; 100 μg/ml lambda vector EcoRI arms; 10 μg/ml cDNA; and 200 U/ml T4 DNA ligase. This mixture was incubated for 3 hours at room temperature. The cDNA/lambda gt-11 ligation was packaged into infectious lambda phage particles as described above.

EXAMPLE 14
A. Antibody Screening of Lambda gt-11 Library

E. coli strain Y1090 was used as the host for lambda phage infections and was maintained on LB/ampicillin plates consisting of: 1% tryptone (w/v); 0.5% yeast extract (w/v); 0.5% NaCl (w/v); 1.5% agar (w/v); the pH was adjusted to 7.5 before autoclaving, and 100 μg/ml ampicillin added after autoclaving. Cultures were grown for phage infection by incubating a single colony overnight on a rotary shaker at 37° C. in 3 ml LB/maltose broth consisting of: 1% tryptone(w/v); 0.5% yeast extract(w/v); 0.5% NaCl(w/v) and 0.2% maltose(w/v).

B. Pretreatment of Antisera

Antisera were treated with an E. coli lysate prior to screening so as to decrease cross-reaction to E. coli protein. E. coli lysate was prepared from Y1090 cells grown overnight in LB broth at 37° C. on a rotary shaker at 220 rpm. Cells were pelleted by centrifugation at 10,000×g at 4° C. and resuspended in 3 ml Lysate Buffer (50 mM Tris pH 8.0 and 10 mM EDTA). Cells were frozen in a dry ice/ethanol bath and thawed at room temperature; the freeze/thaw process was repeated. The suspension was sonicated 5×10 seconds at output control 4 on a constant duty cycle using a Branson Sonifier 450. Cells were placed on ice for 10 seconds after each pulse. Protein concentration in the lysate was estimated using the Bradford Assay (Bio-Rad) according to the manufacturer's suggestion. Sonicated lysate was stored at −20° C. until needed. The antisera was diluted 10-fold with TBST plus 1% dried milk(w/v) and mixed with 1/20 volume E. coli lysate. This solution was incubated at room temperature on a rotary shaker for two hours.

C. Screening of Lambda Gt-11 Phage Plaques

Recombinant phage diluted to 6×10$^3$ pfu in 100 μl of SM was added to 600 μl of an overnight culture of E. coli Y1090 and absorbed at 37° C. for 30 minutes. The cells were then added to 7.5 ml of a 47° C. solution of LB Top Agarose/MgSO$_4$ (0.1% tryptone(w/v); 0.5% yeast extract(w/v); 0.5% NaCl(w/v); 10 mM MgSO$_4$) and plated on a 140 mm LB agar plate. The plate was incubated at 42° C. for approximately 5 hours until tiny plaques were visible. The plate was then overlaid with a 137 mm nitrocellulose filter which had been saturated with a 10 mM solution of IPTG (isopropyl-B-D-thiogalactopyranoside) and air-dried. Incubation of the plate was continued overnight at 37° C. The filter was removed and washed 3 times for 15 minutes each. All washes were carried out at room temperature on a rotary shaker in TBST. The filters were blocked in TBST plus 5% w/v dried milk (Carnation instant non-fat dried milk) for 30 minutes at room temperature on a rotary shaker. Filters were washed 3×15 minutes and then incubated with a 1:1000 dilution of goat anti-rabbit IgG alkaline phosphatase conjugate (Bio-Rad) in TBST plus 1% dried milk(w/v) for 2 hours. The filters were washed 3×15 minutes and then developed in AP buffer (100 mM Tris pH 9.5; 100 mM NaCl; 5 mM MgCl$_2$) to which was added NBT (nitroblue tetrazolium) to a final concentration of 0.33 mg/ml and BCIP (5-bromo-4-chloro-3-indoyl phosphate) to a final concentration of 0.165 mg/ml for 2–5 minutes. The color reaction was stopped by washing the filters with water. Positive plaques were picked to 1 ml SM plus 10 μl chloroform and stored at 4° C. until needed.

Positive plaques were further purified until all the plaques on a filter were positive. Purification rounds were done on 100 mm LB/agar plates with phage titer adjusted to approximately 100 pfu/plate. Positive plaques were confirmed by screening with an affinity-purified antibody at a dilution of 1:100.

EXAMPLE 15
Preparation of Lambda DNA

Phage were adsorbed to 1.5 ml of an overnight culture of E. coli Y1090 at a multiplicity of infection of 0.01 for 30 minutes at 37° C. and then added to 300 ml LB media. The cells were incubated at 37° C. on a rotary shaker about 6 hours (until the cells lysed). One ml chloroform was added to complete the lysis. Cell debris was pelleted by centrifugation at 10,000×g for 10 minutes at 4° C. Lysate was stored at 4° C. until needed.

Lysate was treated with DNase I (final concentration 1 μg/ml) and RNase H (final concentration 5 μg/ml) at 37° C. for one hour. Phage were pelleted by centrifugation for 90 minutes at 27,000 rpm in a Sorvall AH-629 rotor; and the tubes were inverted to drain. Phage pellets were resuspended in 200 μl 0.05M Tris, pH 8 and were extracted with 200 μl Tris-saturated phenol by vigorous shaking for 20 minutes. The mixture was spun in a microcentrifuge, and the aqueous layer saved. The aqueous layer was extracted with phenol and then extracted twice with 200 μl chloroform. DNA was precipitated with 0.1 volume 3M sodium acetate and 6 volumes ethanol at room temperature. DNA was pelleted in a microcentrifuge, washed with 70% ethanol, dried and resuspended in 100 μl TE pH 8.0 (10 mM Tris; 1 mM EDTA).

EXAMPLE 16
Screening of EMBL3 Genomic Library

The EMBL3 genomic library was plated for screening with $^{32}$P-labeled DNA probes. Approximately 10,000 plaques were plated and transferred to nitrocellulose for hybridizations. Filters were prehybridized for 2 hours and hybridized overnight in hybridization buffer in the presence of a DNA probe labeled with $^{32}$P-dCTP (Oligolabeling Kit, Pharmacia). For the selection of EMBL-1, the DNA probe consisted of the EcoRI cDNA insert of lambda gt-11 2-9 which was identified using the antibody to the 235 kD protein. Filters were washed using the protocol employed for Southern hybridizations, and positive plaques were identified after an overnight exposure to film. DNA from positive EMBL-3 phage was prepared as described.

EXAMPLE 17
Sequencing Strategy and Analysis

A series of overlapping subclones from the genomic EMBL1 clone, which contained the triol PKS gene, were constructed in M13mp18 and M13mp19. Nested deletions of some of the clones were obtained using the Cyclone I Biosystem (International Biotechnologies, Inc., New Haven, Conn.). Single stranded DNA was purified by precipitation with 20% polyethylene glycol-2.5M NaCl followed by phenol extraction and ethanol precipitation. The nucleotide sequence of both strands of the DNA was determined using the USB Sequenase Version 2.0 DNA Sequencing Kit (United States Biochemicals, Cleveland, Ohio). The −40 sequencing primer from the kit or custom synthesized oligonucleotides were used to prime the reactions. Regions containing GC compressions were resequenced using dITP in place of dGTP. The sequencing reactions were separated on 6% polyacrylamide denaturing gels. The genomic M13 clones were resequenced using a 373A DNA Sequencer (Applied Biosystems, Inc.) for verification. Introns were identified by sequence analysis of cDNA. The RNA was prepared from a 16 hr culture grown in GP9 medium, and cDNA was synthesized using AMV reverse transcriptase. Custom synthesized oligonucleotides were used to amplify short overlapping stretches of the cDNA by PCR. The PCR conditions, reagents, and product purification were performed as described for PCR with genomic DNA in the PCR/Sequencing Kit PCR Amplification Module manual (Applied Biosystems, Inc., Foster City, Calif.). The PCR were performed using a Perkin Elmer GeneAmp PCR system 9600. The PCR products were sequenced as described in the Taq DyeDeoxy Terminator Cycle Sequencing Kit manual (Applied Biosystems, Inc.), and sequencing reactions were analyzed using the 373A DNA Sequencer. All sequence analyses and manipulations were performed using GeneWorks (IntelliGenetics, Inc., Mt. View, Calif.) on a Macintosh computer (Apple Computer, Inc., Cupertino, Calif.).

EXAMPLE 18

A. Construction of pTPKS100

The transformation vector pTPKS100 contains the polyketide synthase gene responsible for the synthesis of the nonaketide backbone of the triol structure, the phleomycin resistance gene for selection in *A. terreus* and the ampicillin resistance gene for selection in *E. coli*.

The vector was constructed from the pUT715 vector (Cayla, Toulouse Cedex, France) which contains the phleomycin resistance marker from *S. hindustanus* and the termination sequence from the Cyc1 gene in *S. cerevisiae*. The pUT715 vector was digested with BamHI and EcoRv. The β-tubulin gene promoter was inserted in front of the phleomycin marker gene as follows. The β-tubulin promoter was removed from pTL113 by digestion with EcoRI, filling with Klenow fragment, and releasing the fragment from the vector with a BglII digest. The β-promoter was ligated into the pUT715 vector to form pCLS7. The β-tubulin promoter, phleomycin marker and Cyc1 terminator were removed from PCLS7 by digestion with NdeI and BglII followed by filling in the sites, and ligating into the SmaI site of the Bluescript vector (Strategene). This vector was named pLOA.

The polyketide synthase gene was inserted into pLOA in a two step process. The promoter and 5'-end of the PKS gene was obtained from EMBL-1 as a KpnI to EcoRI fragment and ligated into pLOA which had been digested with KpnI and EcoRI. This vector was named TPKS A. The 3' end of the PKS gene was then added to the construction by digesting TPKS A with EcoRI and ligating in the 3' EcoRI gene fragment isolated from EMBL-1. The resulting vector was named pTPKS100.

Transformation of a lovastatin-nonproducing strain with pTPKS100 restored lovastatin production. Transformation of ATCC 20542 (a lovastatin-producing strain) increased lovastatin production relative to untransformed cells.

EXAMPLE 19

Transformation of *A. terreus* ATCC 20542

To determine whether increasing the copy number of the PKS gene in a lovastatin-producing strain would result in an increase in the amount of lovastatin produced, a set of experiments were designed and carried out using the *A. terreus* ATCC 20542. ATCC 20542 was transformed with pTPKS-100. Transformants were checked by PCR to confirm that they contained the phleomycin marker and were true transformants. Following single spore isolation, the confirmed transformants were fermented and lovastatin production was measured by HPLC. The highest producer of single isolates, strain 3-17-7#7, was 32% greater for the transformant than for the parent.

EXAMPLE 20

Characterization of the TPKS Protein Sequence

Splicing of the introns from the DNA sequence and translation of the 9114 nucleotide open reading frame results in a protein of 3038 amino acids with a molecular weight of 269,090 daltons. The final amino acid sequence of the TPKS protein is shown in FIGS. 2A–2C. The features discussed below are presented with their amino acid position noted in the following table.

TPKS PROTEIN FEATURES

| Description | Motif | Amino Acid |
| --- | --- | --- |
| Keto-acyl synthase | Cysteine | 181 |
| Acetyl/Malonyl Transferase | GXSXG | 654-658 |
| Dehydratase | HXXXGXXXXP | 985-994 |
| Methyl Transferase | GXGXG | 1446-1450 |
| Enoyl Reductase | SXGXXS | 1932-1937 |
| Keto Reductase | LXGXXG | 2164-2169 |
| Acyl Carrier Protein | Serine | 2498 |

Inspection of the TPKS amino acid sequence for active site residues and motifs known to be associated with polyketide synthases and fatty acid synthase (FAS) activities resulted in the identification of candidates for expected functional sites. These sites were identified by carrying out searches for amino acid sequences and amino acid homologies using the Intelligenetics Gene Works program. A graphic view of the open reading frame of the protein and the overall placement of the TPKS peptide sequences obtained by partial sequence analysis of TPKS peptides and PKS activities established by alignments and is shown in the figures. Except for the presence of a methyl transferase, not present in FAS, the succession of activities on the TPKS protein is the same as that observed for the rat FAS protein. The alignments carried out on regions of the TPKS, the rat FAS, and the 6-methylsalicyclic acid synthase (6-MSAS) of *Penicillium patulin* in order to identify the best candidate for each of the activities are also presented in the figures.

EXAMPLE 21

Identification of the Keto Acyl Synthase Region

The most 5' site is the β-keto acyl synthase (KAS), also known as the condensing enzyme. This activity is centered around the active site cysteine to which the acyl chain is attached prior to the entry and condensation of the incoming acyl unit. The region shown in the Keto Acyl Synthase Alignment figure contains 30% homology when compared to both the rat FAS and 6-MSAS sequences. However, the TPKS KAS region is most closely related to the rat FAS sequence, exhibiting 49% homology over this region compared to 41% to 6-MSAS.

EXAMPLE 22

Identification of the Acetyl Malonyl Transferase

Proceeding towards the COOH terminus, the next functional site identified is the acetyl/malonyl transferase, which is responsible for accepting the incoming substrate for transfer to either the active thiol of the beta-keto synthase (if a priming acetyl unit) or to the active site thiol of the ACP-pantetheine-SH if a malonyl building block. The identification of the acetyl/malonyl transferase site was found by searching for the GXSXG motif found in many proteins with an active site serine (Wakil, S. J., 1989, *Biochemistry*, 28: 4523–4530). The conservation of this motif in the TPKS protein was observed beginning at amino acid 654, as shown in the figures.

EXAMPLE 23
Identification of the Dehydratase

The next site in common with the FAS protein is the dehydrates. The dehydratase motif consistently found not only in the rat FAS, but the 6-MSAS and the erythromycin SU4 as well consist of a "HXXXGXXXXP" sequence (Donadio, S. and Katz, L., 1992, *Gene*, 111, 51–60.). The homology outside of this signature sequence is very weak.

EXAMPLE 24
Identification of the Enoyl and Keto Reductase

The next two activities identified on the rat FAS protein are the enoyl reductase (ER) and keto reductase (KR). In general, the ER and KR are identified by searching for the GXGXXG/A motif which is proposed to represent the pyridine nucleotide binding site in many proteins (Wierenga, R. K. and Hol, W. G. J., 1983, *Nature*, 302, 842–844). An identical match to this motif has been identified in the rat FAS for both the KR and ER (Witkowski, V., et al., 1991, *Eur. J. Biochem.*, 198, 571–579). Inspection of the TPKS protein identified three matches to the motif. The first begins at position 321 between the β-keto synthase and acetyl/malonyl transferase functions. However, this is not considered to be a good candidate for either of the reductase activities due to its 5' position in the protein and because it lies in a region which is highly homologous to rat FAS. The GXGXXG motif is seen again at position 1446–1451, however, this is considered to be part of the methyl transferase domain. The third time the motif occurs is at position 2438 which lies 60 amino acids 5' of the ACP active site serine. A similar GXGXXG motif is seen in the rat FAS at 125 amino acids prior to the ACP and in 6-MSAS 129 amino acids 5' of the ACP. Since candidates for the NAD(P) binding sites of the KR and ER were not observed in the TPKS protein, homology searches were performed between the regions of the rat FAS which contain these sites and similar regions of the TPKS protein.

As shown in the Enoyl Reductase Alignment, the region of the TPKS protein which lies between the dehydratase and the keto reductase and shows the best alignment to the rat FAS enoyl reductase does not bear a strong homology to the GXGXXG motif or to the region in general. A much stronger homology is evident between the ER domain of SU4 of Erythromycin AII and the rat FAS sequence. The Keto Reductase Alignment of the rat FAS and 6-MSAS keto reductase regions with the TPKS shows slightly higher homology, with 6 out of 30 amino acids surrounding the glycine-rich region conserved between all genes and 13 of 30 conserved between TPKS and either FAS or 6-MSAS.

The glycine-rich segment is part of an overall structural motif for pyridine-nucleotide domains in many proteins (Wierenga, ibid.; Scrutton, N. S., et al., 1990, *Nature*, 343, 38–43; Ma, Q., et al., 1992, 267, 22298–22304; Hanukoglu, I., and Gutfinger, T., 1989, *Eur J. Biochem.*, 180, 479–484). This structural motif consists of a beta sheet-turn-alpha helix where the glycine rich region codes for the strong turn signal in the middle. In addition, downstream acidic or basic amino acids are positioned to bind to the phosphate (NADP) or hydroxyl group (NAD) on the 2' ribose position. This is depicted in a Chou Fasman analysis of the secondary structure of horse alcohol dehydrogenase as a model NADP binding protein. The analysis of the structural characteristics using the Chou Fasman algorithm indicate that this structural motif is conserved in the rat FAS ER and KR domains, (Witkowski, A., 1991, *Eur. J. Biochem.*, 198, 571–579). The structural predictions of the amino acid sequence of the TPKS ER and KR, as well as the 6MSAS KR, show variations of the model. All predicted structures show a β sheet leading into a turn region, even when amino acid homologies are not strong. It has been suggested that deviations from the structural model may reflect differences in substrate specificity (Ma, Q., supra). It is possible that these structural variations are important in the programming of the PKS, resulting in different levels of reduction of the beta-keto group during successive cycles of the biosynthesis of the triol precursor. Consistent throughout the alignments are the presence of basic amino acids at position 20 to 23 amino acids from the "glycine rich" regions identified by the homology searches. The structural similarities and the presence of these basic amino acids suggest that these regions do indeed represent the keto and enoyl reductases of the TPKS protein.

EXAMPLE 25
Identification of the Acyl Carrier Protein

The last active site identified by alignment of the rat FAS with the TPKS is the acyl carrier protein (ACP) active site serine which binds the 4'-phosphopantetheine prosthetic group. While only 6 out of 30 amino acids surrounding the active site serine are conserved over TPKS, rat FAS and 6-MSAS, a higher degree of homology (13 of 30 amino acids) is observed between TPKS and either rat FAS or 6-MSAS.

EXAMPLE 26
Identification of the Methyl Transferase

One activity identified within the reading frame of the TPKS protein which is not present in rat FAS is the methyl transferase responsible for transfer of the methyl group from S-adenosylmethionine (SAM) to the polyketide chain at position 6. A comparison of both eucaryotic and procaryotic methyl transferases responsible for the methylation of RNA, DNA, and protein substrates has identified a sequence motif thought to be part of the SAM-binding domain (Ingrosso, D. et al., 1989, *J. Biol. Chem.*, 264, 20131–20139; Wu, G. et al, 1992, *J. Gen. Micro*, 138, 2101–2112). The binding motif and its alignment with the proposed methyl transferase of the TPKS are shown in the figures.

The absence of a methyl group in compactin suggests that the methyl transferase domain may be absent or altered in the compactin PKS.

EXAMPLE 27
A. Transformation of *Monascus ruber*

Cultures of *M. ruber* strains M4681 AND M82121 are grown, spheroplasted and transformed essentially according to the procedures described above. Petri dishes are incubated at 28° C. and 65% humidity for 7–10 days before transformed colonies are picked.

B. Fermentation of Monascus

The transformed cultures are grown aerobically in a medium containing 7% glycerol, 3% glucose, 3% meat extract, 0.8% peptone, 0.2% $NaNO_3$, and 0.1% $MgSO_4 \cdot 7H_2O$ at 25 degrees C. for 10 days (Kimura et al., 1990. "Biosyn. of Monacolins, Conversion of Monacolin J. To Monacolin K (Mevinolin)", *J. of Antibiotics*, Vol. XLIII No. 12, 1621–1622). *M. ruber* M82121 is grown aerobically at 25° C. for 11 days in a medium containing 11% glycerol, 1% glucose, 5% soy bean powder, 0.8% peptone, 0.1% NaNO$_3$, 0.05% Zn(NO$_3$)$_2$, and 0.5% olive oil (pH 6.5) (Endo, et al., "Dihydromonacolin L and Monacolin X, New Metabolites Those Inhibit Cholesterol Biosynthesis", *J. Antibiot.*, Vol. XXXVIII No. 3, 321–327). The culture broth is extracted with a solvent such as methanol or dichloromethane, concentrated and analyzed by methods such as HPLC. By comparison with an untransformed host or a *M. ruber* culture containing pLO9 without the TPKS genes, the TPKS100 containing host or a derivative thereof produces increased levels of lovastatin, triol, monacolin, dihydromonacolin L or monacolin X.

EXAMPLE 28

A. Transformation of *Paecilomyces viridis*

*P. viridis* strain L-63 is grown, spheroplasted and transformed essentially according to the procedures described above. Cells are transformed with pTPKS100 or a derivative thereof. An example of such a derivative is one in which the DNA encoding the methyl transferase activity of the TPKS protein is altered such that an active methyl transferase is not produced. Petri dishes are incubated at 28° C. and 65% humidity for 7–10 days before transformed colonies are picked.

B. Fermentation of Paecilomyces

*P. viridis* L-63 is grown aerobically in a medium containing 7% glycerol, 3% glucose, 3% meat extract, 0.8% peptone, 0.2% NaNO$_3$, and 0.1% MgSO$_4$.7H$_2$O at 25° C. for 4 to 10 days (Kimura et al., supra). The culture broth is extracted with a solvent such as methanol or dichloromethane and concentrated by evaporation if necessary. By comparison with an untransformed host or a *P. viridis* culture containing pLOA without the TPKS genes, the transformed host can be shown to ferment increased levels of ML-236A and compactin.

EXAMPLE 29

A. Transformation of *Penicillium citrinum*

A suitable culture of *P. citrinum* (e.g., Nara, et al., 1993. "Development of a transformation system for the filamentous, ML-236B (compactin)—producing fungus *Penicillium citrinum*". *Curr. Genet.*, 23, 28–32) is transformed with pTPKS100 or an appropriate derivative thereof using conventional methods.

B. Fermentation of *P. citrinum*

The transformed culture is maintained on yeast-malt extract agar slant (4 g/l dextrose, 10 g/l malt extract, 4 g/l yeast extract, agar 20 g/l, pH 7 prior to sterilization). The slant is washed and used to inoculate to flasks containing KF seed medium (10 g/l CaCl$_2$, 5 g/l corn steep liquor, 40 g/l tomato paste, 10 g/l oatmeal, 10 g/l cerelose, 10 ml trace element per liter, pH 6.8; trace elements consist of 1 g FeSO$_4$.7H$_2$1 g MnSO$_4$.4H$_2$O, 25 mg CuCl$_2$.2H$_2$O, 100 mg CaCl$_2$, 56 mg H$_3$BO$_3$, 19 mg (NH$_4$) 6Mo7024.H$_2$O, 200 mg ZnSO$_4$.7H$_2$O in liter of dH$_2$O). The KF seed flasks are incubated for about 3 days at about 28° C. and 220 rpm. Approximately 1.5 ml is used to inoculate 40 ml of LM production medium per 250 ml flask. LM medium contains 20 g/l dextrose, 20 ml/l glycerol, 10 g/l ardamine pH, 20 g/l malt extract, 8 mg/l CoCls.$_6$H$_2$O and 0.25% polyglycol P2000, pH 7.0. After 5 to 10 days at 25° C. on a shaker, the broth is collected, extracted and concentrated. The transformed culture produces more compactin and dihydrocompactin than does the untransformed parent culture.

EXAMPLE 30

Cloning of TPKS cDNA into a Mammalian Expression Vector

TPKS cDNA expression cassettes are ligated at appropriate restriction endonuclease sites to the following vectors containing strong, universal mammalian promoters:

Cassettes containing the TPKS cDNA in the positive orientation with respect to the promoter are ligated into appropriate restriction sites 3' of the promoter and identified by restriction site mapping and/or sequencing. These cDNA expression vectors are introduced into various host cells by standard methods including but not limited to electroporation, or chemical procedures (cationic liposomes, DEAE dextran, calcium phosphate). Transfected cells and cell culture supernatants can be harvested and analyzed for TPKS expression as described below.

Vectors used for mammalian transient expression may be used to establish stable cell lines expressing TPKS.

EXAMPLE 31

Cloning of TPKS cDNA into a Baculovirus Expression Vector for Expression in Insect Cells Baculovirus vectors, which are derived from the genome of the AcNPV virus, are designed to provide high level expression of cDNA in the Sf9 line of insect cells. Recombinant baculoviruses expressing TPKS cDNA are produced essentially by standard methods (*In Vitrogen Maxbac Manual*). The TPKS cDNA constructs are ligated into the polyhedrin gene in a variety of baculovirus transfer vectors including but not limited to pAC360 and the BlueBac vector (In Vitrogen). Recombinant baculoviruses are generated by homologous recombination following co-transfection of the baculovirus transfer vector and linearized AcNPV genomic DNA [Kitts, P. A., *Nuc. Acid. Res.*, 18, 5667 (1990)] into Sf9 cells. Following plaque purification, TPKS expression is measured by the assays described above.

Authentic, enzymatically-active TPKS is found in the cytoplasm of infected cells. Active TPKS is extracted from infected cells under native conditions by hypotonic or detergent lysis.

EXAMPLE 32

Cloning of TPKS cDNA into a yeast expression vector

Recombinant TPKS is produced in the yeast *S. cerevisiae* following the insertion of the optimal TPKS cDNA cistron into expression vectors designed to direct the intracellular or extracellular expression of heterologous proteins. In the case of intracellular expression, vectors such as EmBLyex4 or the like are ligated to the TPKS cistron [Rinas, U. et al., *Biotechnology*, 8, 543–545 (1990); Horowitz B. et al., *J. Biol. Chem.* 265, 4189–4192 (1989)]. For extracellular expression, the TPKS cistron is ligated into yeast expression vectors which fuse a secretion signal (a yeast or mammnalian peptide) to the NH$_2$ terminus of the TPKS protein [Jacobson, M. A., *Gene*, 85, 511–516 (1989); Riett L. and Bellon N., *Biochem.*, 28, 2941–2949 (1989)].

EXAMPLE 33

Use of TPKS for in vitro production of HMG-CoA inhibitors

Recombinant proteins, including complex proteins, can be overexpressed in a heterologous cells (e.g., Roberts et al., 1993, "Heterologous expression in *E. coli* of an intact multienzyme component of the erythromycin-producing polyketide synthase". *Eur J. Biochem*, 214, 305–311). If the recombinant protein is produced in an inclusion body, renaturation of the desired protein is carried out prior to enzymatic assay (Roberts, 1993).

A suitable host cell is transformed with a vector encoding the TPKS gene. The transformed host cell is grown under conditions that permit the expression of TPKS. The expressed TPKS is isolated and partially purified. The recovered active TPKS enzyme can be added to a reaction mixture containing acetyl-CoA or other charged acyl compounds, appropriate cofactors, and buffer. Incubation of the system can result in the formation of HMG-CoA reductase inhibitors.

EXAMPLE 34
Cloning of other PKS genes using TPKS gene

The cross hybridization of the DNA representing portions of the TPKS gene to genomic DNA isolated from other organisms such as *M. ruber* or *P. citrinum*, makes it possible to clone the homologous genes from the parent organisms. To do this, a genomic library of *M. ruber* or *P. citrinum* was constructed from genomic DNA according to conventional methods. Using, for example, an EMBL vector, an EMBL genomic library was prepared, plated and screened by hybridization with a $^{32}$P-labeled DNA probe consisting of the PstI fragment from the TPKS gene. The PstI fragment contains the keto synthase sequence of the gene. Positive plaques were selected and subjected to additional screening until a purified cross-reacting plaque was selected. The DNA contained in the positive clone is further characterized by physical methods such as restriction mapping, Southern hybridization and DNA sequencing. The function of the defined gene is characterized by cloning the gene in an appropriate transformation vector and transforming a lovastatin non-producing strain with the vector. In the case of *M. ruber*, the cross-reacting PKS would be expected to restore production of Monacolin K (lovastatin) while introduction of a functional *P. citrinum* PKS would result in production of compactin.

EXAMPLE 35
Homology of *A. terreus* TPKS to other strains

A large segment of the 5' end of the *A. terreus* TPKS gene containing the keto synthase region was used to look for cross-hybridization of this region to other strains, including *M. ruber, P. citrinum* and *P. brevicompactum*. The homology was examined by Southern analyses with two probes. The Southern showed cross-reaction to all three strains.

The first probe was the PstI fragment, an 800 bps probe which spans the KAS active site. This probe contains intron I 5' of the active site cysteine in addition to the entire KAS region. This probe was used to detect homology in all three strains. *A. terreus* displayed the profile of cross-reacting bands expected from the restriction map. *M. ruber*, another lovastatin-producing organism, and *P. citrinum*, a compactin-producing organism, showed different but strong hybridizations to the probe.

The second probe was a synthetic oligonucleotide probe having the following sequence: 5'GATACGGCATG-CAGCTCGTCGTTGGTTGCCGTTCATCTGGCT GCA3' (SEQ ID NO:3). Although the hybridization signal to this probe was weaker than the hybridization to the first probe, the results confirm the observations made with the PstI fragment.

When a 3' end cDNA probe was used, cross reaction to all three strains was observed. Single cross-reacting bands in many of the digests indicate that only one gene is being detected in the genomic DNA of each strain. These data suggest that *M. ruber* and *P. citrinum* contain a gene with substantial homology to the TPKS gene of *A. terreus*.

EXAMPLE 36
Use of mutagenized TPKS

The DNA encoding TPKS is mutagenized using standard methods to produce an altered TPKS gene. Host cells are transformed with the altered TPKS to produce altered triol polyketides or altered polyketides with therapeutic use. The altered TPKS protein may be isolated and purified.

---

What is claimed is:

1. A purified and isolated DNA molecule encoding a triol polyketide synthase of *Aspergillus terreus* said DNA molecule having a nucleotide sequence set forth in SEQ ID NO:1.

2. An expression vector comprising a DNA molecule of claim 1.

3. A host cell transformed with an expression vector of claim 2.

4. The expression vector of claim 2 which is pTPKS100 (ATCC 69416).

5. A host cell transformed with the expression vector of claim 4.

6. A process for producing HMG-CoA reductase inhibitors, comprising:

(a) transforming a cell with a DNA molecule of claim 1;

(b) cultivating the transformed cell under conditions that permit the expression of the DNA molecule; and (c) recovering the HMG-CoA reductase inhibitor.

7. The process of claim 6 wherein the HMG-CoA reductase inhibitors are selected from the group consisting of lovastatin, triol and compactin.

8. The process of claim 6 wherein said transformed cell is selected from the group consisting of cells of *Aspergillus terreus, Monascus ruber, Penicillum citrinum, Penicillum brevicompactum, Hypomyces chrysospermus, Paecilomyces viridis*, Paecilomyces sp. M2016, Eupenicillium sp. MM603, *Trichoderma longibrachiatum* M6735 and *Trichoderma pseudokoningii* M6828.

9. A method of isolating DNA encoding polyketide synthase, comprising:

(a) hybridizing a DNA of claim 1 to a sample containing DNA encoding polyketide synthase to form a complex; and (b) purifying the complex.

10. The method of claim 9 wherein the sample is derived from a microorganism, the microorganism being selected from the group consisting of *Aspergillus terreus, Monascus ruber, Penicillum citrinum, Penicillum brevicompactum, Hypomyces chrysopermus, Paecilomyces viridis*, Paecilomyces sp. M2016, Eupenicillium sp. MM603, *Trichoderma longibrachiatum*. M6735 and *Trichoderma pseudokoningii* M6828.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 11561 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: TPKS cDNA ( x i ) SEQUENCE DESCRIPTION: SEQ ID NO:1:

```
CTGCAGTCAA  CGGATCACTT  ACCATTGCTG  TCGCCAAAAA  TATCCGTGAT  AATCCCGCTG      60

GCTTCATTGG  CAAGAGGCTT  GACGTACTTG  GGAGCTTGGG  TCTGGAACTG  GTTCATAACC     120

ACCTTGGTGA  TGAGATGTGC  ATCCCTCGTG  ACTTCCTTGA  ATCCATCGAA  TCCGGGAAGA     180

TGAGAGTGAA  AGTCCTGATG  AGAGCACGAA  GATCAGTAAG  TCAGGTCCTC  ACAGCGGAAG     240
```

-continued

```
CAGTTGCAAA GAACGGTGGA CTCCTTACCG TGCCCAAGAA CTTGTACATA CAGAGCTCTT    300
TCATCTTGCG AAACTCATCG GCCATAGAGG AGGGAAGAAT GGTGCAGTAC CCAGAGTCGA    360
CTATGAACCG AATGGGCTTA TCATTTTGCG AGAACCAGCT CTCAATCCAT GACGGTGCAT    420
TCGCATCAAA ATCCCGTTTG GCCCTCATGG TCGTCAGTTC CCACCATGTT TTCGGATTGA    480
ACACCGGCAG ATCAGATCTC CGGCCACTCG AGCACAGGTA AGAAGAAGG CATAGTAGCC    540
CCGCACTGGT AGTGACCAAG GGCGCAAACC ACGAGCCATG TTGCTGCGTG TCATTCCAAG    600
CCAGCGACAG AAGGTGGTGC GGCTGTGTGA GCGCGTCGAC AGTCATGGCT AGGAGACCAG    660
GTGTGGTTGA GGGATAAGAT ATCGAGAGTG ATGTGAGCAA AAGATCCGGG AAAGGTCGCG    720
AAGGAAAGGG CGTCTCTCTT ACCAAGAAAG TCTGTTCCCT ATCATGCAAT CACCGCTTGC    780
TGTACGGTGG TGATGATGCT GGGATGGTGG TGGGTCCCCA CCGAATAACG CCGGACAGCT    840
GTTGAAGCCG AATGACGCCG GCAGGCCAAA AGAACCCTAC CTTCACTTAC TCAATCGGCG    900
CTTCCCCTCC TATCACCAAA TCGGATGTAA ATGGACGGGC CTTAATAGCG ACCGGCCGGG    960
CCGGGAATCC CCAAACGTAG ATAGATAGGC ATAGACCCGA AATCTTTGGC CCGGCATACA   1020
TGAGCACAGG AAGTTTCACG CGACGGCGCC TTTCCTGCCT CAGCTTCAAT CCAAGCTCAC   1080
GAGTTCTGTC GCCTCTATCA GTCGTGCAAT TGTCCTACTG CAAACAGCAT GGCTCAATCT   1140
ATGTATCCTA ATGAGCCTAT TGTCGTGGTC GGCAGTGGTT GTCGCTTCCC TGGTGACGCC   1200
AACACACCCT CCAAGCTCTG GGAGCTACTC CAGCATCCTC GCGATGTGCA GAGTCGAATC   1260
CCCAAAGAAC GATTTGACGT CGACACATTT TATCACCCGG ACGGGAAGCA CCACGGGCGA   1320
ACAAATGCAC CCTACGCCTA TGTTCTCCAA GACGATCTGG GCGCCTTCGA TGCGGCCTTC   1380
TTCAATATCC AGGCTGGAGA GGCCGAGAGT ATGGACCCCC AGCACCGGCT GTTGCTGGAG   1440
ACGGTGTACG AGGCCGTAAC GAATGCTGGA ATGCGTATCC AGGATCTGCA GGGAACTTCG   1500
ACTGCTGTTT ACGTCGGGGT GATGACGCAC GACTATGAGA CTGTCTCAAC CCGCGACCTG   1560
GAGAGCATCC CCACCTACTC GGCGACGGGT GTCGCGGTCA GTGTTGCGTC CAACCGCATC   1620
TCGTATTTTT TTGACTGGCA TGGACCAAGT GTAAGTCACC CAATATCGTG TAGCAGTCTA   1680
ATCATGCTCT AACGGACCGG GATGGTTGAA AGATGACGAT CGATACGGCA TGCAGCTCGT   1740
CGTTGGTTGC CGTTCATCTG GCGGTGCAAC AGCTACGGAC GGGTCAAAGC TCCATGGCAA   1800
TTGCTGCGGG TGCGAATCTG ATTCTGGGGC CCATGACATT CGTCCTTGAA AGCAAATTGA   1860
GCATGCTATC CCCCTCGGGT CGATCCCGCA TGTGGGACGC CGGAGCTGAC GGCTATGCCA   1920
GAGGCGTGAG TGTTTCTTGA GCTCGTAGAT GACAGTTCCC ATCGCTGACC GTGATCAGGA   1980
AGCTGTTTGC TCTGTAGTGT TGAAGACATT GAGTCAAGCC TTGCGCGATG GGACACGAT    2040
TGAATGTGTC ATCCGAGAAA CTGGGGTGAA TCAAGATGGC CGAACGACCG GAATTACGAT   2100
GCCGAACCAT AGTGCTCAGG AGGCACTCAT CAAGGCTACC TACGCCCAGG CTGGCCTTGA   2160
CATCACCAAG GCCGAGGACA GGTGCCAATT CTTCGAGGCT CATGGTCAGC AAAGAGAACC   2220
TGTTCTGTTG GCGCCCTGCA GCTGACATTC GTATGATAGG GACTGGTACT CCGGCCGGAG   2280
ATCCCCAGGA GGCGGAGGCC ATTGCAACAG CCTTCTTCGG CCACGAGCAG GTAGCACGCA   2340
GCGACGGAAA CGAGAGGGCC CCTCTGTTCG TGGGCAGTGC GAAAACTGTT GTCGGGCACA   2400
CCGAGGGCAC GGCCGGTCTG GCTGGTCTCA TGAAGGCGTC GTTCGCTGTC CGCCATGGGG   2460
TAATCCCCCC CAACCTGCTG TTCGACAAAA TCAGCCCGCG AGTCGCCCCA TTCTATAAAA   2520
ACCTGAGGAT TCCGACAGAA GCTACCCAAT GGCCAGCTCT CCCACCCGGA CAACCGCGCC   2580
GCGCCAGTGT CAACTCCTTT GGTAAGCGAG GATTGCCCGG AGGAACCCTC ACAAGTACTC   2640
```

```
GAATTAATGC  TAACTGAACC  GCGCCGATGG  ACAGGATTCG  GCGGCACGAA  TGCGCATGCC  2700
ATTATTGAGG  AATACATGGA  GCCAGAGCAA  AACCAGCTGC  GAGTCTCGAA  TAATGAGGAC  2760
TGCCCACCCA  TGACCGGTGT  CCTGAGTTTA  CCCTTAGTCC  TCTCGGCGAA  GTCCAGCGC   2820
TCCTTAAAGA  TAATGATGGA  GGAGATGCTG  CAATTCCTTC  AGTCTCACCC  CGAGATACAC  2880
TTGCACGACC  TCACCTGGTC  CTTACTGCGC  AAGCGGTCAG  TTCTACCCTT  CCGCCGGGCT  2940
ATTGTCGGCC  ATAGTCATGA  AACCATCCGC  CGGGCTTTGG  AGGATGCCAT  CGAGGATGGT  3000
ATTGTGTCGA  GCGACTTCAC  TACGGAGGTC  AGAGGCCAGC  CATCGGTGTT  GGGAATCTTC  3060
ACCGGGCAGG  GGGCGCAGTG  GCCGGGGATG  TTAAAGAATC  TGATAGAGGC  ATCGCCATAT  3120
GTGCGGAACA  TAGTGAGGGA  GCTGGACGAC  TCCCTGCAGA  GCTTGCCGGA  AAAATACCGG  3180
CCCTCGTGGA  CGCTACTGGA  CCAGTTCATG  CTAGAAGGAG  AGGCCTCCAA  CGTCCAATAT  3240
GCTACTTTCT  CCCAGCCATT  ATGCTGCGCG  GTGCAAATTG  TCCTGGTCCG  TCTCCTTGAA  3300
GCCGCGAGAA  TACGATTCAC  GGCTGTTGTT  GGACATAGCT  CCGGCGAAAT  TGCTTGCGCC  3360
TTTGCTGCCG  GGCTCATCAG  TGCCTCGTTG  GCGATTCGGA  TTGCTTACTT  ACGTGGAGTC  3420
GTCTCGGCAG  GGGGCGCCAG  AGGCACACCG  GGAGCCATGT  TGGCCGCCGG  GATGTCCTTT  3480
GAGGAAGCAC  AAGAGATCTG  CGAGTGGAT   GCCTTTGAGG  GCCGCATCTG  CGTGGCTGCC  3540
AGCAATTCCC  CAGACAGTGT  AACTTTCTCT  GGCGACGCGA  ACGCAATTGA  TCACCTGAAG  3600
GGCATGTTGG  AGGATGAGTC  CACTTTTGCG  AGACTGCTCA  AGGTCGATAC  AGCGTACCAC  3660
TCGCATCATA  TGCTTCCATG  TGCAGACCCA  TATATGCAAG  CCCTAGAAGA  GTGTGGTTGT  3720
GCTGTTGCCG  ATGCAGGTTC  CCCAGCCGGA  AGTGTACCCT  GGTATTCGTC  CGTGGACGCC  3780
GAGAACAGGC  AAATGGCAGC  AAGAGACGTG  ACCGCCAAGT  ACTGGAAAGA  TAACTTAGTA  3840
TCTCCGGTGC  TATTCTCCCA  CGCAGTGCAG  CGGGCAGTCG  TCACGCACAA  GGCGCTGGAT  3900
ATCGGGATTG  AAGTGGGCTG  TCACCCAGCT  CTCAAGAGCC  CATGCGTCGC  CACCATCAAG  3960
GATGTCCTAT  CTGGGGTTGA  CCTGGCGTAT  ACAGGTTGCT  TGGAGCGAGG  AAAGAATGAT  4020
CTCGATTCAT  TCTCTCGAGC  ACTGGCATAT  CTCTGGGAAA  GGTTTGGTGC  CTCCAGTTTC  4080
GATGCGGACG  AGTTCATGCG  TGCAGTCGCG  CCTGATCGGC  CCTGTATGAG  TGTGTCGAAG  4140
CTCCTACCGG  CCTATCCATG  GGACCGCTCT  CGTCGCTACT  GGGTGGAATC  CCGAGCAACT  4200
CGCCACCATC  TTCGAGGGCC  CAAGCCCCAT  CTTCTATTAG  GAAAGCTCTC  CGAATACAGC  4260
ACTCCGCTAA  GCTTCCAGTG  GCTGAATTTT  GTGCGCCCAC  GAGACATTGA  ATGGCTTGAT  4320
GGACATGCAT  TGCAAGGCCA  GACTGTCTTC  CCTGCGGCCG  GCTATATCGT  CATGGCAATG  4380
GAAGCAGCCT  TAATGATTGC  TGGCACCCAC  GCAAAGCAGG  TCAAGTTACT  GGAGATCTTG  4440
GATATGAGCA  TTGACAAGGC  GGTGATATTT  GACGACGAAG  ACAGCTTGGT  TGAGCTCAAC  4500
CTGACAGCTG  ACGTGTCTCG  CAACGCCGGC  GAAGCAGGTT  CAATGACCAT  AAGCTTCAAG  4560
ATCGATTCCT  GTCTATCGAA  GGAGGGTAAC  CTATCCCTAT  CAGCCAAGGG  CCAACTGGCC  4620
CTAACGATAG  AAGATGTCAA  TCCCAGGACG  ACTTCCGCTA  GCGACCAGCA  CCATCTTCCC  4680
CCGCCAGAAG  AGGAACATCC  TCATATGAAC  CGTGTCAACA  TCAATGCTTT  CTACCACGAG  4740
CTGGGGTTGA  TGGGGTACAA  CTACAGTAAG  GACTTCCGGC  GTCTCCATAA  CATGCAACGA  4800
GCAGATCTTC  GAGCCAGCGG  CACCTTAGAC  TTCATTCCTC  TGATGGACGA  GGGTAATGGC  4860
TGTCCTCTCC  TGCTGCATCC  TGCATCATTG  GACGTCGCCT  TCCAGACTGT  CATCGGCGCA  4920
TACTCCTCCC  CAGGTGATCG  GCGTCTACGC  TGTCTGTATG  TACCCACTCA  CGTTGATCGC  4980
ATCACACTTG  TCCCATCCCT  TTGCCTGGCA  ACGGCTGAGT  CCGGATGCGA  GAAGGTTGCC  5040
```

```
TTCAATACTA  TCAATACGTA  CGACAAGGGA  GACTACTTGA  GCGGTGACAT  TGTGGTGTTT    5100

GACGCGGAGC  AGACCACCCT  GTTCCAGGTT  GAAAATATTA  CTTTTAAGCC  CTTTTCACCC    5160

CCGGATGCTT  CAACTGACCA  TGCGATGTTT  GCCCGATGGA  GCTGGGGTCC  GTTGACTCCG    5220

GACTCGCTGC  TGGATAACCC  GGAGTATTGG  GCCACCGCGC  AGGACAAGGA  GGCGATTCCT    5280

ATTATCGAAC  GCATCGTCTA  CTTCTATATC  CGATCGTTCC  TCAGTCAGCT  TACGCTGGAG    5340

GAGCGCCAGC  AGGCAGCCTT  CCATTTGCAG  AAGCAGATCG  AGTGGCTCGA  ACAAGTCCTG    5400

GCCAGCGCCA  AGGAGGGTCG  TCACCTATGG  TACGACCCCG  GGTGGGAGAA  TGATACTGAG    5460

GCCCAGATTG  AGCACCTTTG  TACTGCTAAC  TCCTACCACC  CTCATGTTCG  CCTGGTTCAG    5520

CGAGTCGGCC  AACACCTGCT  CCCCACCGTA  CGATCGAACG  GCAACCCATT  CGACCTTCTG    5580

GACCACGATG  GGCTCCTGAC  GGAGTTCTAT  ACCAACACAC  TCAGCTTCGG  ACCCGCACTA    5640

CACTACGCCC  GGGAATTGGT  GGCGCAGATC  GCCCATCGCT  ATCAGTCAAT  GGATATTCTG    5700

GAGATTGGAG  CAGGGACCGG  CGGCGCTACC  AAGTACGTGT  TGGCCACGCC  CCAGCTGGGG    5760

TTCAACAGCT  ACACATACAC  CGATATCTCC  ACCGGATTCT  TCGAGCAAGC  GCGGGAGCAA    5820

TTTGCCCCCT  TCGAGGACCG  GATGGTGTTT  GAACCCCTCG  ATATCCGCCG  CAGTCCCGCC    5880

GAGCAGGGCT  TCGAGCCGCA  TGCCTATGAT  CTGATCATTG  CCTCCAATGT  GCTACATGCG    5940

ACACCCGACC  TAGAGAAAAC  CATGGCTCAC  GCCCGCTCTC  TGCTCAAGCC  TGGAGGCCAG    6000

ATGGTTATTC  TGGAGATTAC  CCACAAAGAA  CACACACGGC  TCGGGTTTAT  CTTTGGTCTG    6060

TTCGCCGACT  GGTGGGCTGG  GGTGGATGAT  GGTCGCTGCA  CTGAGCCGTT  TGTCTCGTTC    6120

GACCGCTGGG  ATGCGATCCT  AAAGCGTGTC  GGGTTTTCCG  GTGTGGACAG  TCGCACCACG    6180

GATCGGGACG  CAAATCTATT  CCCGACCTCT  GTGTTTAGTA  CCCATGCAAT  TGACGCCACC    6240

GTGGAGTACT  TAGACGCGCC  GCTTGCCAGC  AGCGGCACCG  TCAAGGACTC  TTACCCTCCC    6300

TTGGTGGTGG  TAGGAGGGCA  GACCCCCCAA  TCTCAGCGTC  TCCTGAACGA  TATAAAAGCG    6360

ATCATGCCTC  CTCGTCCGCT  CCAGACATAC  AAGCGCCTCG  TGGATTTGCT  AGACGCGGAG    6420

GAGCTGCCGA  TGAAGTCCAC  GTTTGTCATG  CTCACGGAGC  TGGACGAGGA  ATTATTCGCC    6480

GGGCTCACTG  AAGAGACCTT  CGAGGCAACC  AAGCTGCTGC  TCACGTACGC  CAGCAATACG    6540

GTCTGGCTGA  CAGAAAATGC  CTGGGTCCAA  CATCCTCACC  AGGCGAGCAC  GATCGGCATG    6600

CTACGCTCCA  TCCGCCGGGA  GCATCCTGAC  TTGGGAGTTC  ATGTTCTGGA  CGTCGACGCG    6660

GTTGAAACCT  TCGATGCAAC  CTTCCTGGTT  GAACAGGTGC  TTCGGCTTGA  GGAGCATACG    6720

GATGAGCTGG  CCAGTTCAAC  TACATGGACT  CAAGAACCCG  AGGTCTCCTG  GTGTAAAGGC    6780

CGCCCGTGGA  TTCCTCGTCT  GAAGCGCGAT  CTGGCTCGCA  ATAACCGAAT  GAACTCCTCG    6840

CGCCGTCCCA  TATACGAGAT  GATCGATTCG  TCGCGGGCTC  CCGTGGCATT  ACAGACGGCT    6900

CGGGATTCAT  CATCCTACTT  CTTGGAGTCC  GCTGAAACCT  GGTTTGTGCC  TGAGAGTGTT    6960

CAGCAGATGG  AAACAAAGAC  GATCTATGTC  CACTTTAGCT  GTCCCCATGC  GCTTAGGGTC    7020

GGACAGCTCG  GGTTTTTCTA  TCTTGTGCAG  GGTCACGTCC  AGGAGGGCAA  TCGCGAAGTG    7080

CCCGTCGTGG  CCTTAGCAGA  GCGTAACGCA  TCCATTGTGC  ACGTTCGTCC  CGATTATATA    7140

TATACTGAGG  CAGATAACAA  TCTGTCTGAG  GGTGGTGGCA  GCCTTATGGT  AACCGTCCTC    7200

GCCGCGGCGG  TGTTGGCGGA  GACGGTGATC  AGTACCGCCA  AGTGCCTGGG  GGTAACTGAC    7260

TCAATCCTCG  TTCTGAATCC  CCCCAGCATA  TGTGGGCAGA  TGTTGCTCCA  TGCTGGTGAA    7320

GAGATCGGTC  TTCAAGTTCA  TCTGGCCACC  ACTTCTGGCA  ACAGGAGTTC  GGTTTCTGCT    7380

GGAGACGCCA  AGTCCTGGCT  AACATTGCAT  GCTCGCGACA  CGGACTGGCA  CCTGCGACGG    7440
```

```
GTACTGCCCC GGGGTGTCCA GGCTTTAGTC GACTTATCAG CCGACCAGAG CTGTGAAGGT    7500
TTGACTCAGA GGATGATGAA AGTTCTGATG CCTGGCTGTG CCCATTACCG TGCGGCAGAC    7560
CTGTTCACAG ACACCGTTTC CACTGAATTG CATAGCGGAT CGCGGCATCA AGCTTCACTG    7620
CCCGCCGCAT ATTGGGAGCA TGTGGTATCC TTAGCCCGCC AGGGACTTCC TAGTGTCAGC    7680
GAGGGGTGGG AGGTGATGCC GTGCACTCAA TTTGCAGCGC ATGCCGACAA GACGCGCCCG    7740
GATCTCTCGA CAGTTATTTC CTGGCCCCGG GAGTCGGACG AGGCTACGCT TCCTACCAGG    7800
GTTCGCTCCA TTGACGCTGA GACCCTCTTT GCGGCCGACA AAACATATCT CCTGGTCGGA    7860
CTGACTGGAG ATCTTGGACG ATCACTAGGT CGTTGGATGG TCCAGCATGG GGCCTGCCAC    7920
ATTGTACTTA CGAGCAGAAA TCCGCAGGTG AACCCCAAGT GGCTGGCGCA TGTTAAGAA     7980
CTGGGTGGTC GAGTCACTGT TCTTTCCATG TAAGAGGAGT CCTTCCTTCT GCAATTCCTC    8040
CTTATGATCC CGACTAACGC AGCTGGCTTC AGGGACGTGA CAAGCCAAAA CTCAGTGGAA    8100
GCTGGCCTGG CTAAACTCAA GGATCTGCAT CTGCCACCAG TGGGGGTAT TGCCTTTGGC     8160
CCTCTGGTTC TGCAGGATGT GATGCTAAAT AATATGGAAC TGCCAATGAT GGAGATGGTG    8220
CTCAACCCCA AGGTCGAAGG CGTCCGCATC CTGCACGAGA AGTTCTCCGA TCCGACCAGT    8280
AGCAACCCTC TCGACTTCTT CGTGATGTTC TCCTCGATTG TGGCCGTCAT GGGCAACCCG    8340
GGTCAGGCTA ACTACAGTGC GGCTAACTGC TACCTTCAAG CGCTGGCGCA GCAGCGAGTT    8400
GCATCCGGAT TAGCAGTACG TTTTCACTCC ATCCTTTGCT AAACACTCCT ATGGGCCTTT    8460
ACTAAACCGG GCAGGCGTCC ACCATCGACA TCGGTGCCGT GTACGGCGTT GGGTTCGTCA    8520
CTCGGGCGGA GCTGGAGGAG GACTTTAATG CAATTCGGTT CATGTTCGAT TCGGTTGAGG    8580
AACATGAACT GCATACACTG TTTGCTGAGG CAGTGGTGGC CGGTCGACGA GCCGTGCACC    8640
AGCAAGAGCA GCAGCGGAAG TTCGCGACAG TGCTCGACAT GGCTGATCTG GAACTGACAA    8700
CCGGAATTCC GCCCCTGGAT CCAGCCCTCA AAGATCGGAT CACCTTCTTC GACGACCCCC    8760
GCATAGGCAA CTTAAAAATT CCGGAGTACC GAGGGGCCAA AGCAGGCGAA GGGGCAGCCG    8820
GCTCCAAGGG CTCGGTCAAA GAACAGCTCT TGCAGGCGAC GAACCTGGAC CAGGTCCGTC    8880
AGATCGTCAT CGGTAAGTTG AGCGAATCCG GGAATATTC TCCCCTTCCT CACTCAGCGG     8940
ACTGGAGATT AACCGCTTCT TTTCCTTTGG CAGATGGACT CTCCGCGAAG CTGCAGGTGA    9000
CCCTGCAGAT CCCCGATGGG GAAAGCGTGC ATCCCACCAT CCCACTAATC GATCAGGGGG    9060
TGGACTCTCT GGGCGCGGTC ACCGTGGGAA CCTGGTTCTC CAAGCAGCTG TACCTTGATT    9120
TGCCACTCCT GAAAGTGCTT GGGGGTGCTT CGATCACCGA TCTCGCTAAT GAGGCTGCTG    9180
CGCGATTGCC ACCTAGCTCC ATTCCCCTCG TCGCAGCCAC CGACGGGGGT GCAGAGAGCA    9240
CTGACAATAC TTCCGAGAAT GAAGTTTCGG GACGCGAGGA TACTGACCTT AGTGCCGCCG    9300
CCACCATCAC TGAGCCCTCG TCTGCCGACG AAGACGATAC GGAGCCGGGC GACGAGGACG    9360
TCCCGCGTTC CCACCATCCA CTGTCTCTCG GGCAAGAATA CTCCTGGAGA ATCCAGCAGG    9420
GAGCCGAAGA CCCCACCGTC TTTAACAACA CCATTGGTAT GTTCATGAAG GGCTCTATTG    9480
ACCTTAAACG GCTGTACAAG GCGTTGAGAG CGGTCTTGCG CCGCCACGAG ATCTTCCGCA    9540
CGGGGTTTGC CAACGTGGAT GAGAACGGGA TGGCCCAGCT GGTGTTTGGT CAAACCAAAA    9600
ACAAAGTCCA GACCATCCAA GTGTCTGACC GAGCCGGCGC CGAAGAGGGC TACCGACAAC    9660
TGGTGCAGAC ACGGTATAAC CCTGCCGCAG GAGACACCTT GCGGCTGGTG GACTTCTTCT    9720
GGGGCCAGGA CGACCATCTG CTGGTTGTGG CTTACCACCG ACTCGTCGGG GATGGATCTA    9780
CTACAGAGAA CATCTTCGTC GAAGCGGGCC AGCTCTACGA CGGCACGTCG CTAAGTCCAC    9840
```

| | | | | | | |
|---|---|---|---|---|---|---|
| ATGTCCCTCA | GTTTGCGGAC | CTGGCGGCAC | GGCAACGCGC | AATGCTCGAG | GATGGGAGAA | 9900 |
| TGGAGGAGGA | TCTCGCGTAC | TGGAAGAAAA | TGCATTACCG | ACCGTCCTCA | ATTCCAGTGC | 9960 |
| TCCCACTGAT | GCGGCCCCTG | GTAGGTAACA | GTAGCAGGTC | CGATACTCCA | AATTTCCAGC | 10020 |
| ACTGTGGACC | CTGGCAGCAG | CACGAAGCCG | TGGCGCGACT | TGATCCGATG | GTGGCCTTCC | 10080 |
| GCATCAAGGA | GCGCAGTCGC | AAGCACAAGG | CGACGCCGAT | GCAGTTCTAT | CTGGCGGCGT | 10140 |
| ATCAGGTGCT | GTTGGCGCGC | CTCACCGACA | GCACCGATCT | CACCGTGGGC | CTCGCCGACA | 10200 |
| CCAACCGTGC | GACTGTCGAC | GAGATGGCGG | CCATGGGGTT | CTTCGCCAAC | CTCCTTCCCC | 10260 |
| TGCGCTTCCG | GGATTTCCGC | CCCCATATAA | CGTTTGGCGA | GCACCTTATC | GCCACCCGTG | 10320 |
| ACCTGGTGCG | TGAGGCCTTG | CAGCACGCCC | GCGTGCCCTA | CGGCGTCCTC | CTCGATCAAC | 10380 |
| TGGGGCTGGA | GGTCCCGGTC | CCGACCAGCA | ATCAACCTGC | GCCTTTGTTC | CAGGCCGTCT | 10440 |
| TCGATTACAA | GCAGGGCCAG | GCGGAAAGTG | GAACGATTGG | GGGTGCCAAG | ATAACCGAGG | 10500 |
| TGATTGCCAC | GCGCGAGCGC | ACCCCTTACG | ATGTCGTGCT | GGAGATGTCG | GATGATCCCA | 10560 |
| CCAAGGATCC | GCTGCTCACG | GCCAAGTTAC | AGAGTTCCCG | CTACGAGGCT | CACCACCCTC | 10620 |
| AAGCCTTCTT | GGAGAGCTAC | ATGTCCCTTC | TCTCTATGTT | CTCGATGAAT | CCCGCCCTGA | 10680 |
| AGCTGGCATG | ATGGCGCAAA | CATAGAACAT | GATAGCGCAG | CAGGGACGAT | GTAGATAGAG | 10740 |
| CTTTGCTTCT | GCGGGTGGAT | CTATAATATA | GTATATATAA | ATATGGTGAG | CCGAACGAAG | 10800 |
| AGGGGGGAAT | GCCACAATTA | TTTACTGTTT | TGCGCCGTAC | ACGAGGAGAA | GACGTCCAGA | 10860 |
| ACAACATAAA | TATATCACTC | TAGTGAGACA | CCATATATTC | GGAGAGACTA | TAAAAATATA | 10920 |
| CATCTACTCC | AATGTCTGGG | CCGTCACACA | CAGCTTACGA | AAACGATTAA | TGACCTCCAA | 10980 |
| CACGTCGCGC | GGTCGATTGG | GAAACTGATG | CTGCCCAGCA | AACTCCAATA | CCTGCGCCTC | 11040 |
| TCGGGGGGAG | AAATGGCGCG | CCACCAGCAT | CTTCGATCCT | GCGAGCGCAA | AATCATCGCG | 11100 |
| ACCCTGCAGA | TGTAATGTCG | GTATCCGAAT | GACCAGTTCC | TCCTGCCACT | CGGTATCTTT | 11160 |
| GCTGTCGTTG | TCGTCGTCAT | GGTTCTTCAT | CATTCGTTCC | TCATATACTG | GCTTGCCTCG | 11220 |
| TCTTGATACC | AGGGACAGAT | CAACAGCGCA | ACACTCATCC | GGGGCAACCA | GGGCAGGTGA | 11280 |
| CCCATCTGCT | GCTGCCAGAG | GAGCAAGGTC | GTCACCAGGG | CACCTTCGGA | GAAACCGATA | 11340 |
| GCACCCACGA | TAGGGATGTG | GGGGTGTTGA | GTCTGCCAGT | CGACAATGGT | GCGGCGGATG | 11400 |
| GGGTCGTGGA | CGGCGGCGAG | GCGTTCGCTC | ACGGAGGGTC | CATTATGATT | GTTGTCGCTG | 11460 |
| CTGCTTTCAA | ACCAGGAGTA | ATATGGCCCT | AGGTCGGCGA | AGACGGGGAG | AATCCCAGGC | 11520 |
| CCTGCAGAGG | AAGGGAACGG | AGCTGTCACG | TAGACGAATT | C | | 11561 |

( 2 ) INFORMATION FOR SEQ ID NO:2:

( i ) SEQUENCE CHARACTERISTICS:
        ( A ) LENGTH: 3038 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( v i ) ORIGINAL SOURCE:
        ( A ) ORGANISM: TPKS Protein ( x i ) SEQUENCE DESCRIPTION: SEQ ID NO:2:

```
Met  Ala  Gln  Ser  Met  Tyr  Pro  Asn  Glu  Pro  Ile  Val  Val  Val  Gly  Ser
 1                 5                        10                       15
```

```
Gly  Cys  Arg  Phe  Pro  Gly  Asp  Ala  Asn  Thr  Pro  Ser  Lys  Leu  Trp  Glu
               20                  25                       30

Leu  Leu  Gln  His  Pro  Arg  Asp  Val  Gln  Ser  Arg  Ile  Pro  Lys  Glu  Arg
                    35                  40                  45

Phe  Asp  Val  Asp  Thr  Phe  Tyr  His  Pro  Asp  Gly  Lys  His  His  Gly  Arg
     50                       55                       60

Thr  Asn  Ala  Pro  Tyr  Ala  Tyr  Val  Leu  Gln  Asp  Asp  Leu  Gly  Ala  Phe
65                       70                       75                            80

Asp  Ala  Ala  Phe  Phe  Asn  Ile  Gln  Ala  Gly  Glu  Ala  Glu  Ser  Met  Asp
                         85                  90                            95

Pro  Gln  His  Arg  Leu  Leu  Leu  Glu  Thr  Val  Tyr  Glu  Ala  Val  Thr  Asn
                    100                 105                      110

Ala  Gly  Met  Arg  Ile  Gln  Asp  Leu  Gln  Gly  Thr  Ser  Thr  Ala  Val  Tyr
               115                 120                      125

Val  Gly  Val  Met  Thr  His  Asp  Tyr  Glu  Thr  Val  Ser  Thr  Arg  Asp  Leu
     130                      135                      140

Glu  Ser  Ile  Pro  Thr  Tyr  Ser  Ala  Thr  Gly  Val  Ala  Val  Ser  Val  Ala
145                      150                      155                           160

Ser  Asn  Arg  Ile  Ser  Tyr  Phe  Phe  Asp  Trp  His  Gly  Pro  Ser  Met  Thr
                    165                      170                      175

Ile  Asp  Thr  Ala  Cys  Ser  Ser  Ser  Leu  Val  Ala  Val  His  Leu  Ala  Val
               180                      185                      190

Gln  Gln  Leu  Arg  Thr  Gly  Gln  Ser  Ser  Met  Ala  Ile  Ala  Ala  Gly  Ala
               195                      200                      205

Asn  Leu  Ile  Leu  Gly  Pro  Met  Thr  Phe  Val  Leu  Glu  Ser  Lys  Leu  Ser
     210                      215                      220

Met  Leu  Ser  Pro  Ser  Gly  Arg  Ser  Arg  Met  Trp  Asp  Ala  Gly  Ala  Asp
225                      230                      235                           240

Gly  Tyr  Ala  Arg  Gly  Glu  Ala  Val  Cys  Ser  Val  Val  Leu  Lys  Thr  Leu
               245                      250                      255

Ser  Gln  Ala  Leu  Arg  Asp  Gly  Asp  Thr  Ile  Glu  Cys  Val  Ile  Arg  Glu
               260                      265                      270

Thr  Gly  Val  Asn  Gln  Asp  Gly  Arg  Thr  Thr  Gly  Ile  Thr  Met  Pro  Asn
               275                      280                      285

His  Ser  Ala  Gln  Glu  Ala  Leu  Ile  Lys  Ala  Thr  Tyr  Ala  Gln  Ala  Gly
     290                      295                      300

Leu  Asp  Ile  Thr  Lys  Ala  Glu  Asp  Arg  Cys  Gln  Phe  Phe  Glu  Ala  His
305                      310                      315                           320

Gly  Thr  Gly  Thr  Pro  Ala  Gly  Asp  Pro  Gln  Glu  Ala  Glu  Ala  Ile  Ala
                    325                      330                      335

Thr  Ala  Phe  Phe  Gly  His  Glu  Gln  Val  Ala  Arg  Ser  Asp  Gly  Asn  Glu
               340                      345                      350

Arg  Ala  Pro  Leu  Phe  Val  Gly  Ser  Ala  Lys  Thr  Val  Val  Gly  His  Thr
          355                      360                      365

Glu  Gly  Thr  Ala  Gly  Leu  Ala  Gly  Leu  Met  Lys  Ala  Ser  Phe  Ala  Val
     370                      375                      380

Arg  His  Gly  Val  Ile  Pro  Pro  Asn  Leu  Leu  Phe  Asp  Lys  Ile  Ser  Pro
385                      390                      395                           400

Arg  Val  Ala  Pro  Phe  Tyr  Lys  Asn  Leu  Arg  Ile  Pro  Thr  Glu  Ala  Thr
                    405                      410                      415

Gln  Trp  Pro  Ala  Leu  Pro  Pro  Gly  Gln  Pro  Arg  Arg  Ala  Ser  Val  Asn
               420                      425                      430

Ser  Phe  Gly  Phe  Gly  Gly  Thr  Asn  Ala  His  Ala  Ile  Ile  Glu  Glu  Tyr
               435                      440                      445
```

| | | | | | | | | | | | | | | |
|---|---|---|---|---|---|---|---|---|---|---|---|---|---|---|
| Met | Glu | Pro | Glu | Gln | Asn | Gln | Leu | Arg | Val | Ser | Asn | Asn | Glu | Asp | Cys |
| | 450 | | | | 455 | | | | | 460 | | | | | |
| Pro | Pro | Met | Thr | Gly | Val | Leu | Ser | Leu | Pro | Leu | Val | Leu | Ser | Ala | Lys |
| 465 | | | | | 470 | | | | | 475 | | | | | 480 |
| Ser | Gln | Arg | Ser | Leu | Lys | Ile | Met | Met | Glu | Met | Leu | Gln | Phe | Leu | |
| | | | | 485 | | | | | 490 | | | | | 495 | |
| Gln | Ser | His | Pro | Glu | Ile | His | Leu | His | Asp | Leu | Thr | Trp | Ser | Leu | Leu |
| | | | 500 | | | | | 505 | | | | | 510 | | |
| Arg | Lys | Arg | Ser | Val | Leu | Pro | Phe | Arg | Arg | Ala | Ile | Val | Gly | His | Ser |
| | | 515 | | | | | 520 | | | | | 525 | | | |
| His | Glu | Thr | Ile | Arg | Arg | Ala | Leu | Glu | Asp | Ala | Ile | Glu | Asp | Gly | Ile |
| | 530 | | | | 535 | | | | | 540 | | | | | |
| Val | Ser | Ser | Asp | Phe | Thr | Thr | Glu | Val | Arg | Gly | Gln | Pro | Ser | Val | Leu |
| 545 | | | | | 550 | | | | | 555 | | | | | 560 |
| Gly | Ile | Phe | Thr | Gly | Gln | Gly | Ala | Gln | Trp | Pro | Gly | Met | Leu | Lys | Asn |
| | | | | 565 | | | | | 570 | | | | | 575 | |
| Leu | Ile | Glu | Ala | Ser | Pro | Tyr | Val | Arg | Asn | Ile | Val | Arg | Glu | Leu | Asp |
| | | | 580 | | | | | 585 | | | | | 590 | | |
| Asp | Ser | Leu | Gln | Ser | Leu | Pro | Glu | Lys | Tyr | Arg | Pro | Ser | Trp | Thr | Leu |
| | | 595 | | | | | 600 | | | | | 605 | | | |
| Leu | Asp | Gln | Phe | Met | Leu | Glu | Gly | Glu | Ala | Ser | Asn | Val | Gln | Tyr | Ala |
| | 610 | | | | 615 | | | | | 620 | | | | | |
| Thr | Phe | Ser | Gln | Pro | Leu | Cys | Cys | Ala | Val | Gln | Ile | Val | Leu | Val | Arg |
| 625 | | | | | 630 | | | | | 635 | | | | | 640 |
| Leu | Leu | Glu | Ala | Ala | Arg | Ile | Arg | Phe | Thr | Ala | Val | Val | Gly | His | Ser |
| | | | | 645 | | | | | 650 | | | | | 655 | |
| Ser | Gly | Glu | Ile | Ala | Cys | Ala | Phe | Ala | Ala | Gly | Leu | Ile | Ser | Ala | Ser |
| | | | 660 | | | | | 665 | | | | | 670 | | |
| Leu | Ala | Ile | Arg | Ile | Ala | Tyr | Leu | Arg | Gly | Val | Val | Ser | Ala | Gly | Gly |
| | | 675 | | | | | 680 | | | | | 685 | | | |
| Ala | Arg | Gly | Thr | Pro | Gly | Ala | Met | Leu | Ala | Ala | Gly | Met | Ser | Phe | Glu |
| | 690 | | | | 695 | | | | | 700 | | | | | |
| Glu | Ala | Gln | Glu | Ile | Cys | Glu | Leu | Asp | Ala | Phe | Glu | Gly | Arg | Ile | Cys |
| 705 | | | | | 710 | | | | | 715 | | | | | 720 |
| Val | Ala | Ala | Ser | Asn | Ser | Pro | Asp | Ser | Val | Thr | Phe | Ser | Gly | Asp | Ala |
| | | | | 725 | | | | | 730 | | | | | 735 | |
| Asn | Ala | Ile | Asp | His | Leu | Lys | Gly | Met | Leu | Glu | Asp | Glu | Ser | Thr | Phe |
| | | | 740 | | | | | 745 | | | | | 750 | | |
| Ala | Arg | Leu | Leu | Lys | Val | Asp | Thr | Ala | Tyr | His | Ser | His | His | Met | Leu |
| | | 755 | | | | | 760 | | | | | 765 | | | |
| Pro | Cys | Ala | Asp | Pro | Tyr | Met | Gln | Ala | Leu | Glu | Glu | Cys | Gly | Cys | Ala |
| | 770 | | | | 775 | | | | | 780 | | | | | |
| Val | Ala | Asp | Ala | Gly | Ser | Pro | Ala | Gly | Ser | Val | Pro | Trp | Tyr | Ser | Ser |
| 785 | | | | | 790 | | | | | 795 | | | | | 800 |
| Val | Asp | Ala | Glu | Asn | Arg | Gln | Met | Ala | Ala | Arg | Asp | Val | Thr | Ala | Lys |
| | | | | 805 | | | | | 810 | | | | | 815 | |
| Tyr | Trp | Lys | Asp | Asn | Leu | Val | Ser | Pro | Val | Leu | Phe | Ser | His | Ala | Val |
| | | | 820 | | | | | 825 | | | | | 830 | | |
| Gln | Arg | Ala | Val | Val | Thr | His | Lys | Ala | Leu | Asp | Ile | Gly | Ile | Glu | Val |
| | | 835 | | | | | 840 | | | | | 845 | | | |
| Gly | Cys | His | Pro | Ala | Leu | Lys | Ser | Pro | Cys | Val | Ala | Thr | Ile | Lys | Asp |
| | 850 | | | | 855 | | | | | 860 | | | | | |
| Val | Leu | Ser | Gly | Val | Asp | Leu | Ala | Tyr | Thr | Gly | Cys | Leu | Glu | Arg | Gly |

-continued

| 865 | | | 870 | | | 875 | | | 880 |

Lys Asn Asp Leu Asp Ser Phe Ser Arg Ala Leu Ala Tyr Leu Trp Glu
                    885                 890                 895

Arg Phe Gly Ala Ser Ser Phe Asp Ala Asp Glu Phe Met Arg Ala Val
                900                 905                 910

Ala Pro Asp Arg Pro Cys Met Ser Val Ser Lys Leu Leu Pro Ala Tyr
                915                 920                 925

Pro Trp Asp Arg Ser Arg Arg Tyr Trp Val Glu Ser Arg Ala Thr Arg
        930                 935                 940

His His Leu Arg Gly Pro Lys Pro His Leu Leu Gly Lys Leu Ser
945                 950                 955                 960

Glu Tyr Ser Thr Pro Leu Ser Phe Gln Trp Leu Asn Phe Val Arg Pro
                965                 970                 975

Arg Asp Ile Glu Trp Leu Asp Gly His Ala Leu Gln Gly Gln Thr Val
                980                 985                 990

Phe Pro Ala Ala Gly Tyr Ile Val Met Ala Met Glu Ala Leu Met
        995                 1000                1005

Ile Ala Gly Thr His Ala Lys Gln Val Lys Leu Leu Glu Ile Leu Asp
        1010                1015                1020

Met Ser Ile Asp Lys Ala Val Ile Phe Asp Glu Asp Ser Leu Val
1025                1030                1035                1040

Glu Leu Asn Leu Thr Ala Asp Val Ser Arg Asn Ala Gly Glu Ala Gly
                1045                1050                1055

Ser Met Thr Ile Ser Phe Lys Ile Asp Ser Cys Leu Ser Lys Glu Gly
                1060                1065                1070

Asn Leu Ser Leu Ser Ala Lys Gly Gln Leu Ala Leu Thr Ile Glu Asp
                1075                1080                1085

Val Asn Pro Arg Thr Thr Ser Ala Ser Asp Gln His His Leu Pro Pro
                1090                1095                1100

Pro Glu Glu Glu His Pro His Met Asn Arg Val Asn Ile Asn Ala Phe
1105                1110                1115                1120

Tyr His Glu Leu Gly Leu Met Gly Tyr Asn Tyr Ser Lys Asp Phe Arg
                1125                1130                1135

Arg Leu His Asn Met Gln Arg Ala Asp Leu Arg Ala Ser Gly Thr Leu
                1140                1145                1150

Asp Phe Ile Pro Leu Met Asp Glu Gly Asn Gly Cys Pro Leu Leu Leu
                1155                1160                1165

His Pro Ala Ser Leu Asp Val Ala Phe Gln Thr Val Ile Gly Ala Tyr
        1170                1175                1180

Ser Ser Pro Gly Asp Arg Arg Leu Arg Cys Leu Tyr Val Pro Thr His
1185                1190                1195                1200

Val Asp Arg Ile Thr Leu Val Pro Ser Leu Cys Leu Ala Thr Ala Glu
                1205                1210                1215

Ser Gly Cys Glu Lys Val Ala Phe Asn Thr Ile Asn Thr Tyr Asp Lys
        1220                1225                1230

Gly Asp Tyr Leu Ser Gly Asp Ile Val Val Phe Asp Ala Glu Gln Thr
        1235                1240                1245

Thr Leu Phe Gln Val Glu Asn Ile Thr Phe Lys Pro Phe Ser Pro Pro
        1250                1255                1260

Asp Ala Ser Thr Asp His Ala Met Phe Ala Arg Trp Ser Trp Gly Pro
1265                1270                1275                1280

Leu Thr Pro Asp Ser Leu Leu Asp Asn Pro Glu Tyr Trp Ala Thr Ala
                1285                1290                1295

```
Gln  Asp  Lys  Glu  Ala  Ile  Pro  Ile  Ile  Glu  Arg  Ile  Val  Tyr  Phe  Tyr
              1300                     1305                    1310

Ile  Arg  Ser  Phe  Leu  Ser  Gln  Leu  Thr  Leu  Glu  Glu  Arg  Gln  Gln  Ala
     1315                    1320                    1325

Ala  Phe  His  Leu  Gln  Lys  Gln  Ile  Glu  Trp  Leu  Glu  Gln  Val  Leu  Ala
          1330                    1335                         1340

Ser  Ala  Lys  Glu  Gly  Arg  His  Leu  Trp  Tyr  Asp  Pro  Gly  Trp  Glu  Asn
1345                     1350                    1355                         1360

Asp  Thr  Glu  Ala  Gln  Ile  Glu  His  Leu  Cys  Thr  Ala  Asn  Ser  Tyr  His
                    1365                    1370                    1375

Pro  His  Val  Arg  Leu  Val  Gln  Arg  Val  Gly  Gln  His  Leu  Leu  Pro  Thr
                    1380                    1385                         1390

Val  Arg  Ser  Asn  Gly  Asn  Pro  Phe  Asp  Leu  Leu  Asp  His  Asp  Gly  Leu
               1395                    1400                    1405

Leu  Thr  Glu  Phe  Tyr  Thr  Asn  Thr  Leu  Ser  Phe  Gly  Pro  Ala  Leu  His
                    1410                    1415                    1420

Tyr  Ala  Arg  Glu  Leu  Val  Ala  Gln  Ile  Ala  His  Arg  Tyr  Gln  Ser  Met
1425                     1430                    1435                         1440

Asp  Ile  Leu  Glu  Ile  Gly  Ala  Gly  Thr  Gly  Gly  Ala  Thr  Lys  Tyr  Val
                    1445                    1450                         1455

Leu  Ala  Thr  Pro  Gln  Leu  Gly  Phe  Asn  Ser  Tyr  Thr  Tyr  Thr  Asp  Ile
               1460                    1465                    1470

Ser  Thr  Gly  Phe  Phe  Glu  Gln  Ala  Arg  Glu  Gln  Phe  Ala  Pro  Phe  Glu
               1475                    1480                    1485

Asp  Arg  Met  Val  Phe  Glu  Pro  Leu  Asp  Ile  Arg  Arg  Ser  Pro  Ala  Glu
               1490                    1495                    1500

Gln  Gly  Phe  Glu  Pro  His  Ala  Tyr  Asp  Leu  Ile  Ile  Ala  Ser  Asn  Val
1505                     1510                    1515                         1520

Leu  His  Ala  Thr  Pro  Asp  Leu  Glu  Lys  Thr  Met  Ala  His  Ala  Arg  Ser
                    1525                    1530                    1535

Leu  Leu  Lys  Pro  Gly  Gly  Gln  Met  Val  Ile  Leu  Glu  Ile  Thr  His  Lys
                    1540                    1545                    1550

Glu  His  Thr  Arg  Leu  Gly  Phe  Ile  Phe  Gly  Leu  Phe  Ala  Asp  Trp  Trp
               1555                    1560                    1565

Ala  Gly  Val  Asp  Asp  Gly  Arg  Cys  Thr  Glu  Pro  Phe  Val  Ser  Phe  Asp
1570                     1575                    1580

Arg  Trp  Asp  Ala  Ile  Leu  Lys  Arg  Val  Gly  Phe  Ser  Gly  Val  Asp  Ser
1585                     1590                    1595                         1600

Arg  Thr  Thr  Asp  Arg  Asp  Ala  Asn  Leu  Phe  Pro  Thr  Ser  Val  Phe  Ser
                    1605                    1610                    1615

Thr  His  Ala  Ile  Asp  Ala  Thr  Val  Glu  Tyr  Leu  Asp  Ala  Pro  Leu  Ala
                    1620                    1625                    1630

Ser  Ser  Gly  Thr  Val  Lys  Asp  Ser  Tyr  Pro  Pro  Leu  Val  Val  Val  Gly
               1635                    1640                    1645

Gly  Gln  Thr  Pro  Gln  Ser  Gln  Arg  Leu  Leu  Asn  Asp  Ile  Lys  Ala  Ile
               1650                    1655                    1660

Met  Pro  Pro  Arg  Pro  Leu  Gln  Thr  Tyr  Lys  Arg  Leu  Val  Asp  Leu  Leu
1665                     1670                    1675                         1680

Asp  Ala  Glu  Glu  Leu  Pro  Met  Lys  Ser  Thr  Phe  Val  Met  Leu  Thr  Glu
                    1685                    1690                    1695

Leu  Asp  Glu  Glu  Leu  Phe  Ala  Gly  Leu  Thr  Glu  Glu  Thr  Phe  Glu  Ala
                    1700                    1705                    1710

Thr  Lys  Leu  Leu  Leu  Thr  Tyr  Ala  Ser  Asn  Thr  Val  Trp  Leu  Thr  Glu
               1715                    1720                    1725
```

```
Asn Ala Trp Val Gln His Pro His Gln Ala Ser Thr Ile Gly Met Leu
    1730                1735                1740
Arg Ser Ile Arg Arg Glu His Pro Asp Leu Gly Val His Val Leu Asp
1745                1750                1755                1760
Val Asp Ala Val Glu Thr Phe Asp Ala Thr Phe Leu Val Glu Gln Val
                1765                1770                1775
Leu Arg Leu Glu Glu His Thr Asp Glu Leu Ala Ser Ser Thr Thr Trp
            1780                1785                1790
Thr Gln Glu Pro Glu Val Ser Trp Cys Lys Gly Arg Pro Trp Ile Pro
            1795                1800                1805
Arg Leu Lys Arg Asp Leu Ala Arg Asn Asn Arg Met Asn Ser Ser Arg
        1810                1815                1820
Arg Pro Ile Tyr Glu Met Ile Asp Ser Ser Arg Ala Pro Val Ala Leu
1825                1830                1835                1840
Gln Thr Ala Arg Asp Ser Ser Ser Tyr Phe Leu Glu Ser Ala Glu Thr
                1845                1850                1855
Trp Phe Val Pro Glu Ser Val Gln Gln Met Glu Thr Lys Thr Ile Tyr
            1860                1865                1870
Val His Phe Ser Cys Pro His Ala Leu Arg Val Gly Gln Leu Gly Phe
        1875                1880                1885
Phe Tyr Leu Val Gln Gly His Val Gln Glu Gly Asn Arg Glu Val Pro
        1890                1895                1900
Val Val Ala Leu Ala Glu Arg Asn Ala Ser Ile Val His Val Arg Pro
1905                1910                1915                1920
Asp Tyr Ile Tyr Thr Glu Ala Asp Asn Asn Leu Ser Glu Gly Gly Gly
                1925                1930                1935
Ser Leu Met Val Thr Val Leu Ala Ala Ala Val Leu Ala Glu Thr Val
            1940                1945                1950
Ile Ser Thr Ala Lys Cys Leu Gly Val Thr Asp Ser Ile Leu Val Leu
        1955                1960                1965
Asn Pro Pro Ser Ile Cys Gly Gln Met Leu Leu His Ala Gly Glu Glu
        1970                1975                1980
Ile Gly Leu Gln Val His Leu Ala Thr Thr Ser Gly Asn Arg Ser Ser
1985                1990                1995                2000
Val Ser Ala Gly Asp Ala Lys Ser Trp Leu Thr Leu His Ala Arg Asp
                2005                2010                2015
Thr Asp Trp His Leu Arg Arg Val Leu Pro Arg Gly Val Gln Ala Leu
            2020                2025                2030
Val Asp Leu Ser Ala Asp Gln Ser Cys Glu Gly Leu Thr Gln Arg Met
            2035                2040                2045
Met Lys Val Leu Met Pro Gly Cys Ala His Tyr Arg Ala Ala Asp Leu
        2050                2055                2060
Phe Thr Asp Thr Val Ser Thr Glu Leu His Ser Gly Ser Arg His Gln
2065                2070                2075                2080
Ala Ser Leu Pro Ala Ala Tyr Trp Glu His Val Val Ser Leu Ala Arg
                2085                2090                2095
Gln Gly Leu Pro Ser Val Ser Glu Gly Trp Glu Val Met Pro Cys Thr
            2100                2105                2110
Gln Phe Ala Ala His Ala Asp Lys Thr Arg Pro Asp Leu Ser Thr Val
        2115                2120                2125
Ile Ser Trp Pro Arg Glu Ser Asp Glu Ala Thr Leu Pro Thr Arg Val
        2130                2135                2140
Arg Ser Ile Asp Ala Glu Thr Leu Phe Ala Ala Asp Lys Thr Tyr Leu
```

```
                 2 1 4 5                    2 1 5 0                    2 1 5 5                    2 1 6 0
L e u   V a l   G l y   L e u   T h r   G l y   A s p   L e u   G l y   A r g   S e r   L e u   G l y   A r g   T r p   M e t
                                 2 1 6 5                    2 1 7 0                    2 1 7 5
V a l   G l n   H i s   G l y   A l a   C y s   H i s   I l e   V a l   L e u   T h r   S e r   A r g   A s n   P r o   G l n
                                 2 1 8 0                    2 1 8 5                    2 1 9 0
V a l   A s n   P r o   L y s   T r p   L e u   A l a   H i s   V a l   G l u   G l u   L e u   G l y   G l y   A r g   V a l
                                 2 1 9 5                    2 2 0 0                    2 2 0 5
T h r   V a l   L e u   S e r   M e t   A s p   V a l   T h r   S e r   G l n   A s n   S e r   V a l   G l u   A l a   G l y
         2 2 1 0                             2 2 1 5                                     2 2 2 0
L e u   A l a   L y s   L e u   L y s   A s p   L e u   H i s   L e u   P r o   P r o   V a l   G l y   G l y   I l e   A l a
2 2 2 5                                     2 2 3 0                             2 2 3 5                                     2 2 4 0
P h e   G l y   P r o   L e u   V a l   L e u   G l n   A s p   V a l   M e t   L e u   A s n   A s n   M e t   G l u   L e u
                                     2 2 4 5                                     2 2 5 0                                    2 2 5 5
P r o   M e t   M e t   G l u   M e t   V a l   L e u   A s n   P r o   L y s   V a l   G l u   G l y   V a l   A r g   I l e
                                     2 2 6 0                                     2 2 6 5                                    2 2 7 0
L e u   H i s   G l u   L y s   P h e   S e r   A s p   P r o   T h r   S e r   S e r   A s n   P r o   L e u   A s p   P h e
                             2 2 7 5                                     2 2 8 0                                    2 2 8 5
P h e   V a l   M e t   P h e   S e r   S e r   I l e   V a l   A l a   V a l   M e t   G l y   A s n   P r o   G l y   G l n
                                     2 2 9 0                                     2 2 9 5                                    2 3 0 0
A l a   A s n   T y r   S e r   A l a   A l a   A s n   C y s   T y r   L e u   G l n   A l a   L e u   A l a   G l n   G l n
2 3 0 5                                     2 3 1 0                                     2 3 1 5                              2 3 2 0
A r g   V a l   A l a   S e r   G l y   L e u   A l a   A l a   S e r   T h r   I l e   A s p   I l e   G l y   A l a   V a l
                                 2 3 2 5                                     2 3 3 0                                        2 3 3 5
T y r   G l y   V a l   G l y   P h e   V a l   T h r   A r g   A l a   G l u   L e u   G l u   G l u   A s p   P h e   A s n
                         2 3 4 0                                     2 3 4 5                                     2 3 5 0
A l a   I l e   A r g   P h e   M e t   P h e   A s p   S e r   V a l   G l u   G l u   H i s   G l u   L e u   H i s   T h r
                 2 3 5 5                                     2 3 6 0                                     2 3 6 5
L e u   P h e   A l a   G l u   A l a   V a l   V a l   A l a   G l y   A r g   A r g   A l a   V a l   H i s   G l n   G l n
         2 3 7 0                                     2 3 7 5                                     2 3 8 0
G l u   G l n   G l n   A r g   L y s   P h e   A l a   T h r   V a l   L e u   A s p   M e t   A l a   A s p   L e u   G l u
2 3 8 5                                     2 3 9 0                                     2 3 9 5                              2 4 0 0
L e u   T h r   T h r   G l y   I l e   P r o   P r o   L e u   A s p   P r o   A l a   L e u   L y s   A s p   A r g   I l e
                                 2 4 0 5                                     2 4 1 0                                        2 4 1 5
T h r   P h e   P h e   A s p   A s p   P r o   A r g   I l e   G l y   A s n   L e u   L y s   I l e   P r o   G l u   T y r
                         2 4 2 0                                     2 4 2 5                                     2 4 3 0
A r g   G l y   A l a   L y s   A l a   G l y   G l u   G l y   A l a   A l a   G l y   S e r   L y s   G l y   S e r   V a l
                 2 4 3 5                                     2 4 4 0                                     2 4 4 5
L y s   G l u   G l n   L e u   L e u   G l n   A l a   T h r   A s n   L e u   A s p   G l n   V a l   A r g   G l n   I l e
         2 4 5 0                                     2 4 5 5                                     2 4 6 0
V a l   I l e   A s p   G l y   L e u   S e r   A l a   L y s   L e u   G l n   V a l   T h r   L e u   G l n   I l e   P r o
2 4 6 5                                     2 4 7 0                                     2 4 7 5                              2 4 8 0
A s p   G l y   G l u   S e r   V a l   H i s   P r o   T h r   I l e   P r o   L e u   I l e   A s p   G l n   G l y   V a l
                                 2 4 8 5                                     2 4 9 0                                        2 4 9 5
A s p   S e r   L e u   G l y   A l a   V a l   T h r   V a l   G l y   T h r   T r p   P h e   S e r   L y s   G l n   L e u
                         2 5 0 0                                     2 5 0 5                                     2 5 1 0
T y r   L e u   A s p   L e u   P r o   L e u   L e u   L y s   V a l   L e u   G l y   G l y   A l a   S e r   I l e   T h r
                 2 5 1 5                                     2 5 2 0                                     2 5 2 5
A s p   L e u   A l a   A s n   G l u   A l a   A l a   A l a   A r g   L e u   P r o   P r o   S e r   S e r   I l e   P r o
         2 5 3 0                                     2 5 3 5                                     2 5 4 0
L e u   V a l   A l a   A l a   T h r   A s p   G l y   G l y   A l a   G l u   S e r   T h r   A s p   A s n   T h r   S e r
2 5 4 5                                     2 5 5 0                                     2 5 5 5                              2 5 6 0
G l u   A s n   G l u   V a l   S e r   G l y   A r g   G l u   A s p   T h r   A s p   L e u   S e r   A l a   A l a   A l a
                                 2 5 6 5                                     2 5 7 0                                        2 5 7 5
```

```
Thr Ile Thr Glu Pro Ser Ser Ala Asp Glu Asp Thr Glu Pro Gly
              2580                2585                2590

Asp Glu Asp Val Pro Arg Ser His His Pro Leu Ser Leu Gly Gln Glu
              2595                2600            2605

Tyr Ser Trp Arg Ile Gln Gln Gly Ala Glu Asp Pro Thr Val Phe Asn
    2610                2615                2620

Asn Thr Ile Gly Met Phe Met Lys Gly Ser Ile Asp Leu Lys Arg Leu
2625            2630                2635                    2640

Tyr Lys Ala Leu Arg Ala Val Leu Arg Arg His Glu Ile Phe Arg Thr
              2645                2650                2655

Gly Phe Ala Asn Val Asp Glu Asn Gly Met Ala Gln Leu Val Phe Gly
              2660                2665                2670

Gln Thr Lys Asn Lys Val Gln Thr Ile Gln Val Ser Asp Arg Ala Gly
              2675                2680                2685

Ala Glu Glu Gly Tyr Arg Gln Leu Val Gln Thr Arg Tyr Asn Pro Ala
              2690                2695                2700

Ala Gly Asp Thr Leu Arg Leu Val Asp Phe Phe Trp Gly Gln Asp Asp
2705                2710                2715                2720

His Leu Leu Val Val Ala Tyr His Arg Leu Val Gly Asp Gly Ser Thr
              2725                2730                2735

Thr Glu Asn Ile Phe Val Glu Ala Gly Gln Leu Tyr Asp Gly Thr Ser
              2740                2745                2750

Leu Ser Pro His Val Pro Gln Phe Ala Asp Leu Ala Ala Arg Gln Arg
              2755                2760                2765

Ala Met Leu Glu Asp Gly Arg Met Glu Glu Asp Leu Ala Tyr Trp Lys
              2770                2775                2780

Lys Met His Tyr Arg Pro Ser Ser Ile Pro Val Leu Pro Leu Met Arg
2785                2790                2795                    2800

Pro Leu Val Gly Asn Ser Ser Arg Ser Asp Thr Pro Asn Phe Gln His
              2805                2810                2815

Cys Gly Pro Trp Gln Gln His Glu Ala Val Ala Arg Leu Asp Pro Met
              2820                2825                2830

Val Ala Phe Arg Ile Lys Glu Arg Ser Arg Lys His Lys Ala Thr Pro
              2835                2840                2845

Met Gln Phe Tyr Leu Ala Ala Tyr Gln Val Leu Leu Ala Arg Leu Thr
2850                2855                2860

Asp Ser Thr Asp Leu Thr Val Gly Leu Ala Asp Thr Asn Arg Ala Thr
2865                2870                2875                2880

Val Asp Glu Met Ala Ala Met Gly Phe Phe Ala Asn Leu Leu Pro Leu
              2885                2890                2895

Arg Phe Arg Asp Phe Arg Pro His Ile Thr Phe Gly Glu His Leu Ile
              2900                2905                2910

Ala Thr Arg Asp Leu Val Arg Glu Ala Leu Gln His Ala Arg Val Pro
              2915                2920                2925

Tyr Gly Val Leu Leu Asp Gln Leu Gly Leu Glu Val Pro Val Pro Thr
              2930                2935                2940

Ser Asn Gln Pro Ala Pro Leu Phe Gln Ala Val Phe Asp Tyr Lys Gln
2945                2950                2955                    2960

Gly Gln Ala Glu Ser Gly Thr Ile Gly Gly Ala Lys Ile Thr Glu Val
              2965                2970                2975

Ile Ala Thr Arg Glu Arg Thr Pro Tyr Asp Val Val Leu Glu Met Ser
              2980                2985                2990

Asp Asp Pro Thr Lys Asp Pro Leu Leu Thr Ala Lys Leu Gln Ser Ser
              2995                3000                3005
```

| | | | | | | | | | | | | | | |
|---|---|---|---|---|---|---|---|---|---|---|---|---|---|---|
| Arg | Tyr | Glu | Ala | His | His | Pro | Gln | Ala | Phe | Leu | Glu | Ser | Tyr | Met | Ser |
| | 3010 | | | | | 3015 | | | | | 3020 | | | |
| Leu | Leu | Ser | Met | Phe | Ser | Met | Asn | Pro | Ala | Leu | Lys | Leu | Ala |
| 3025 | | | | | 3030 | | | | | 3035 | | | |

(2) INFORMATION FOR SEQ ID NO:3:

(i) SEQUENCE CHARACTERISTICS:
      (A) LENGTH: 45 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: probe (xi) SEQUENCE DESCRIPTION: SEQ ID NO:3:

GATACGGCAT GCAGCTCGTC GTTGGTTGCC GTTCATCTGG CTGCA     45